(12) United States Patent
Wybo et al.

(10) Patent No.: US 11,980,476 B1
(45) Date of Patent: May 14, 2024

(54) INTRAOPERATIVE NEURAL MONITORING METHOD

(71) Applicant: NEURALYTIX, LLC, Brighton, MI (US)

(72) Inventors: Christopher Wybo, Brighton, MI (US); David S. Nay, Novi, MI (US); Darren P. Scarfe, LaSalle (CA); Lukas T. Scarfe, LaSalle (CA); Samantha J. O'Neil, Windsor (CA); Gary Gordon, Sammamish, WA (US)

(73) Assignee: NEURALYTIX, LLC, Brighton, MI (US)

( * ) Notice: Subject to any disclaimer, the term of this patent is extended or adjusted under 35 U.S.C. 154(b) by 0 days.

(21) Appl. No.: 18/516,647

(22) Filed: Nov. 21, 2023

Related U.S. Application Data

(63) Continuation-in-part of application No. 18/320,450, filed on May 19, 2023, now Pat. No. 11,850,040.

(60) Provisional application No. 63/485,476, filed on Feb. 16, 2023.

(51) Int. Cl.
  *A61B 5/00* (2006.01)
  *A61B 5/11* (2006.01)
  *A61B 90/00* (2016.01)

(52) U.S. Cl.
  CPC .......... *A61B 5/4519* (2013.01); *A61B 5/0048* (2013.01); *A61B 5/1107* (2013.01); *A61B 5/4041* (2013.01); *A61B 5/7246* (2013.01); *A61B 5/725* (2013.01); *A61B 5/7257* (2013.01); *A61B 5/726* (2013.01); *A61B 5/7267* (2013.01); *A61B 5/746* (2013.01); *A61B 90/08* (2016.02); *A61B 2560/06* (2013.01)

(58) Field of Classification Search
  CPC ... A61B 5/1107; A61B 5/4893; A61B 5/7239; A61B 5/726; A61B 5/05; A61N 1/36031
  See application file for complete search history.

(56) References Cited

U.S. PATENT DOCUMENTS

| | | | |
|---|---|---|---|
| 7,277,759 B2 * | 10/2007 | Overstreet | A61B 5/389 607/137 |
| 2019/0247654 A1 * | 8/2019 | Alyagon | A61B 5/377 |
| 2020/0113485 A1 * | 4/2020 | Wybo | A61B 5/1106 |

* cited by examiner

*Primary Examiner* — David J. McCrosky
(74) *Attorney, Agent, or Firm* — Quinn IP Law

(57) ABSTRACT

A method for detecting an artificially induced neuromuscular response in a subject includes receiving a mechanomyography (MMG) output signal from a mechanical sensor in contact with a muscle of the subject; applying one or more conditioning filters to the MMG output signal to generate a conditioned signal and analyzing the conditioned signal to identify one or more candidate waveforms. Each candidate waveform meets one or more analog or digital signal characteristic criteria associated with an artificially induced neuromuscular response. The method then compares a first candidate waveform to a second candidate waveform to determine a degree of similarity between the first and second candidate waveforms, and provides an alert to a user that indicates detection of the artificially induced neuromuscular response when the degree of similarity exceeds a predetermined threshold.

21 Claims, 9 Drawing Sheets

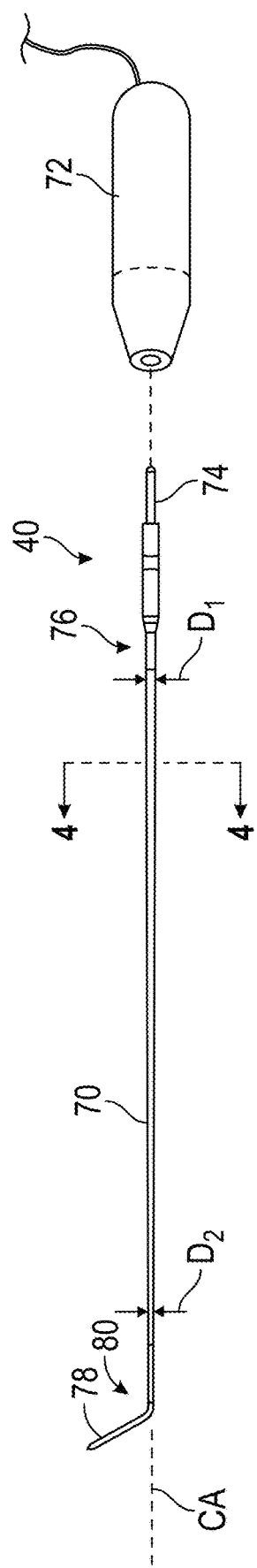
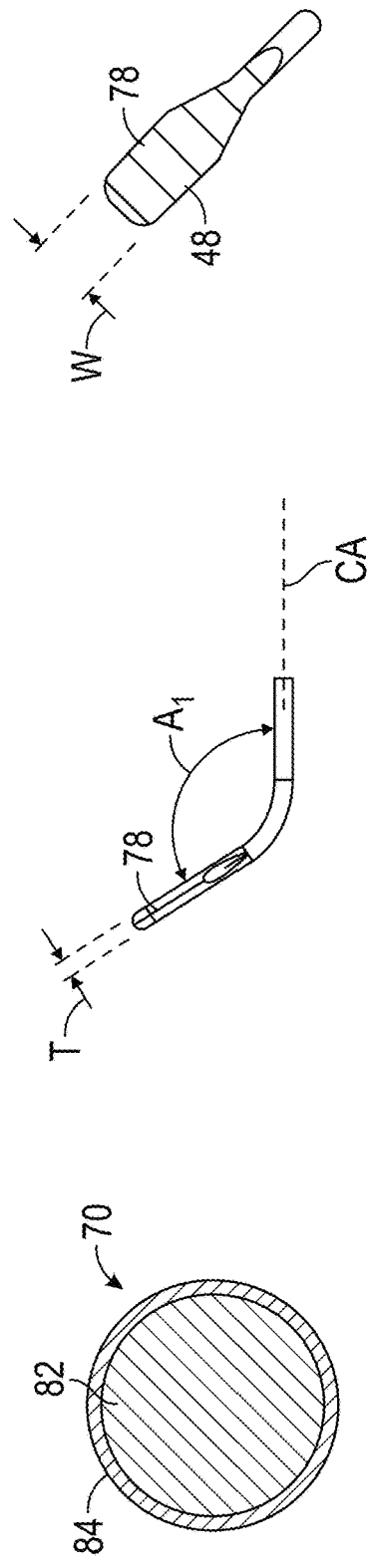
FIG. 3
FIG. 4
FIG. 5
FIG. 6

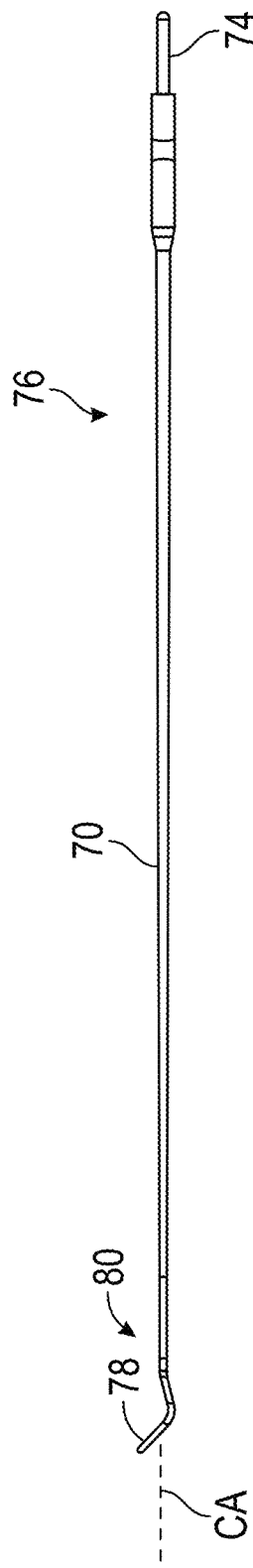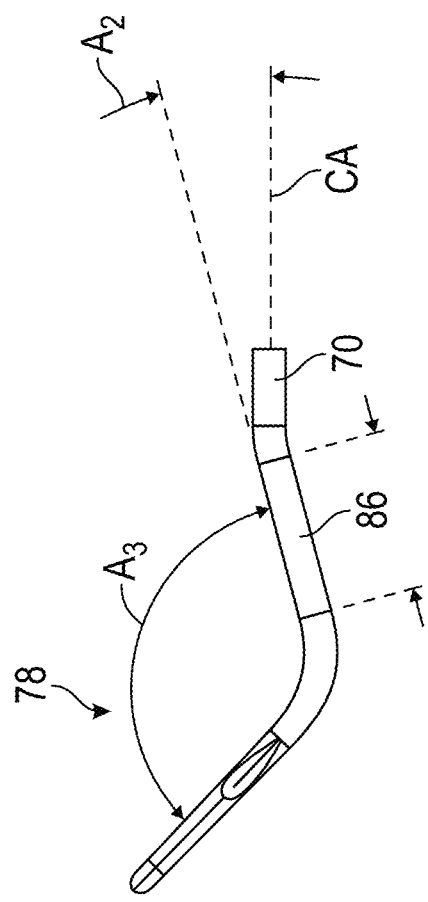
FIG. 7
FIG. 8

INTRAOPERATIVE NEURAL MONITORING METHOD

CROSS-REFERENCE TO RELATED APPLICATIONS

The present disclosure is a continuation-in-part application of and claims the benefit of priority from U.S. patent application Ser. No. 18/320,450, filed 19 May 2023, which claims the benefit of priority from U.S. Provisional Patent No. 63/485,476, filed 16 Feb. 2023. Both applications are incorporated by reference in their entirety and for all that they disclose.

TECHNICAL FIELD

The present disclosure relates generally to systems and techniques for intraoperatively identifying the presence and/or functioning of nerves.

BACKGROUND

Mechanomyography (MMG) is a technique for assessing muscle activity by detecting and analyzing the mechanical vibrations generated by muscle fibers during contraction. MMG has gained increasing attention in recent years as a potential alternative to electromyography (EMG) for evaluating neuromuscular function, as it is less susceptible to certain artifacts and electrical interference that may affect EMG signals.

Despite the potential advantages of MMG, its adoption has been limited, primarily due to challenges associated with MMG signal analysis and interpretation. MMG signals are often complex and may include various environmental or subject-created artifacts and physiological sources of variability that can hinder accurate characterization.

BRIEF DESCRIPTION OF THE DRAWINGS

FIG. 3 is a partially exploded schematic side view of a selectively electrifiable nerve stimulator for applying an electrical stimulus to a nerve or nerve root during a surgical procedure.

FIG. 4 is a schematic cross-sectional view of the nerve stimulator of FIG. 3, taken along line 4-4.

FIG. 5 is a partial side view of the stimulator tip of the nerve stimulator of FIG. 3.

FIG. 6 is a partial top view of the stimulator tip of the nerve stimulator of FIG. 3.

FIG. 7 is schematic side view of a selectively electrifiable nerve stimulator for applying an electrical stimulus to a nerve or nerve root during a surgical procedure.

FIG. 8 is a is a partial side view of the stimulator tip of the nerve stimulator of FIG. 7.

DETAILED DESCRIPTION

Figure 1:
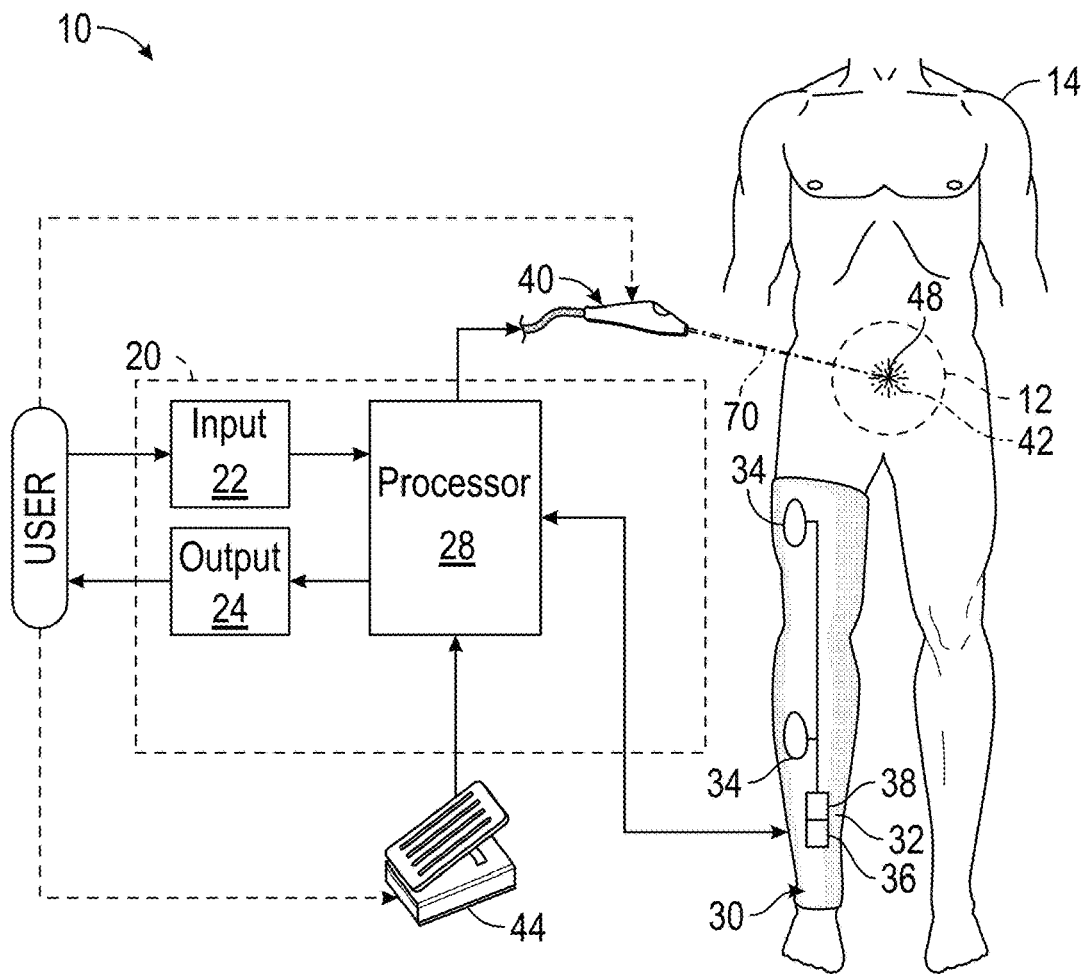
FIG. 1 is a schematic diagram of a neural monitoring system, for detecting an artificially-induced neuromuscular response of a subject during a surgical procedure

Referring to the drawings, wherein like reference numerals are used to identify like or identical components in the various views, FIG. 1 schematically illustrates a neural monitoring system 10 that may have particular use during a surgical procedure. As will be discussed, in some embodiments, the neural monitoring system 10 may be used within some surgical contexts to identify the presence of one or more nerves within an intracorporeal treatment area 12 of a subject 14. Further, in some embodiments, the neural monitoring system 10 may be used to intraoperatively assess the functioning or health of a nerve, such as during a decompression-type surgical procedure.

Regardless of the specific end use, the present neural monitoring system 10 operates by monitoring one or more muscles of the subject 14 for a muscular response that is indicative of a stimulus-induced depolarization of a nerve (i.e., an artificially induced neuromuscular response). If the system 10 detects a response of the muscle to the applied stimulus, then parameters such as the magnitude and waveform of the muscle response, the magnitude and/or timing of the applied stimulus, and/or the context of the procedure may be analyzed to provide intraoperative alerts and/or real-time diagnostics to a surgeon about a state of the procedure or status of a nerve within the patient.

As used herein, an "artificially induced neuromuscular response" is a response of a muscle to an artificial/non-biological stimulus applied to a nerve innervating that muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may cause the nerve to involuntarily depolarize (resulting in a corresponding contraction of the muscle or muscles innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially induced neuromuscular response, a muscle innervated by the artificially depolarized nerve may physically contract or relax (i.e., a mechanical response) and/or the electrical potential throughout the muscle may be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

The neural monitoring system 10 may generally include a host system 20 and one or more sensing devices 30 that coordinate to monitor muscles for a response to a stimulus 42 provided by a stimulator 40. As schematically shown in FIG. 1, the host system 20 may include one or more input devices 22 that are operative to receive information from the surgeon, one or more output devices 24 that are operative to communicate alerts or to provide informational feedback to the surgeon, and a processor 28 that is operative to at least manage the flow of information between the input devices 22, output devices 24, sensing devices 30, and stimulator 40.

In general, the one or more input devices 22 may include a keyboard, a mouse, and/or a digitizer provided with a touch-screen display. These devices may receive pre-operative case information or may permit a surgeon to alter various intraoperative parameters, alarm limits, or other case information before or during a procedure. In some embodiments, the stimulator 40 and/or a foot pedal 44 may provide additional input to the host system 20. This input may be in the form of an analog or digital signal that is indicative of the delivery and/or magnitude of a stimulus. The output device 24 may include, for example, a visual display such as an LED/LCD display, one or more indicator lights, or speakers capable of providing an audible alert to the surgeon. Examples of display screens that may be displayed via the output device 24 are provided in FIGS. 11-12.

Sensing Device

The sensing device 30 is the portion of the system 10 that directly contacts the subject 14 and is responsible for, at a minimum, sensing/detecting responses of the subject's muscles to the applied stimulus. The sensing device 30 may include a carrier material 32 that is operative to be secured to the external skin surface of the subject 14, and at least one neuromuscular sensor (NMS) 34 that is coupled with the carrier material 32 and is operative to monitor a muscular response of the subject 14. In some embodiments, each neuromuscular sensor 34 may include its own carrier material that is operative to mechanically couple the NMS 34 to the skin of the subject. In other embodiments, two or more neuromuscular sensors 34 may be held in mechanical contact with the skin of the subject 14 via a common carrier material 32 such as a large patch or band. Likewise, while the various neuromuscular sensors may each monitor different muscles/muscle groups, in some embodiments, multiple neuromuscular sensors may be joined together via a common wiring harness for the purpose of simplifying the initial setup.

Within the context of the present system 10, the purpose of the carrier material 32 is to hold the one or more neuromuscular sensors 34 in direct mechanical communication with the skin of the subject 14. In some embodiments the carrier material 32 may encapsulate and/or form a sterile barrier around the NMS 34. This may promote cost-effective reusability of the NMS 34 without subjecting it to the same sterilization requirements as if it were directly within the sterile field (i.e., absent a suitable barrier material). Suitable carrier materials may include, for example, adhesive pads, pocketed patches, cuffs, and/or sleeves. In some embodiments, the carrier material 32 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 32 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 32 may include, for example, a blood pressure cuff worn around the subject's arm (or else may include functionality similar to that of a standard blood pressure cuff). In these examples, the carrier material 32 serves a function outside of that of a dedicated neuromuscular sensing device, and thus provides efficiencies in pre-op preparation and planning, while also allowing monitoring access on sometimes crowded limbs.

Figure 2:
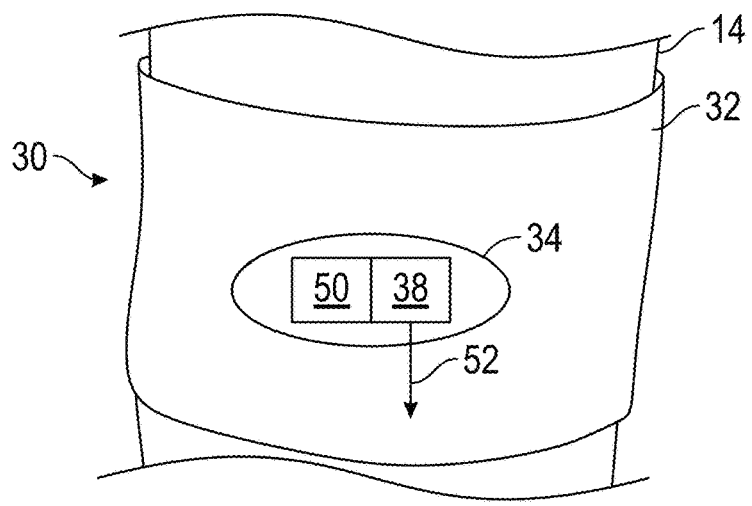
FIG. 2 is a schematic side view of a sensing device for use with a neural monitoring system.

In various embodiments, such as shown in FIG. 2, each NMS 34 may comprise a mechanical sensor 50 that is operative to monitor the relative movement of the muscle that the NMS 34 is most closely coupled with. Such mechanical sensors 50 may include, for example, a strain gauge, a pressure/force transducer, a position encoder, an accelerometer, a piezoelectric material, or any other transducer or combination of transducers that may convert a physical motion into a variable analog or digital electrical signal. In some embodiments, a neuromuscular sensor 34 may alternatively or additionally include one or more transdermal electrodes, needle electrodes, or other such sensors that may be operative to monitor mechanical or electrical response parameters of the subject.

In some embodiments, each neuromuscular sensor 34 (or collection of neuromuscular sensors 34, such as shown in FIG. 1) may include a local processor 38 that is in communication with the mechanical sensor 50 of that NMS 34. Such local processors 38 may be configured to, for example, preprocess and/or filter data acquired from the mechanical sensor 50 and transmit an MMG output signal 52 to the host system 20 (i.e., where the MMG output signal may be representative of the output or filtered output of the mechanical sensor 50). In some configurations these local processors 38 may even be capable of performing event detection algorithms (as will be discussed in greater detail below) to determine if a sensed movement is a result of a stimulus-induced depolarization of a nerve. This local processor 38 may further include suitable communication circuitry to facilitate unidirectional or bidirectional digital communication with the host system 20.

In general, processors used with the present system 10 (e.g., processors 28, 38) may each be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), flash memory, high-speed clocks, analog-to-digital (A/D) circuitry, digital-to-analog (D/A) circuitry, input/output (I/O) circuitry, and/or signal conditioning and buffering electronics.

Stimulator Probe

As noted above, the system 10 may further include one or more elongate medical instruments 40 (i.e., stimulators 40) that are capable of selectively providing a stimulus 42 within the intracorporeal treatment area 12 of the subject 14. For example, in one configuration, the elongate medical instrument 40 may include an elongate body (e.g., a ball-tip probe, k-wire, or needle) that has an electrode 48 disposed on a distal end portion. The electrode 48 may be selectively electrified, at either the request of a user/surgeon, or at the command of the processor 28, to provide an electrical stimulus 42 to intracorporeal tissue of the subject. In other configurations, the elongate medical instrument 40 may comprise a dilator, retractor, clip, cautery probe, pedicle screw, robotic end effector, or any other medical instrument that may be used in an invasive medical procedure. Regardless of the instrument, if the intended artificial stimulus is an electrical current, the instrument 40 may include a selectively electrifiable electrode 48 disposed at a portion of the instrument that is intended to contact tissue within the intracorporeal treatment area 12 during the procedure. In some embodiments, the electrode 48 may be a distinct element, such as a gold contact that is overlaid onto the instrument. In other embodiments, the electrode 48 may simply be an uninsulated/exposed portion of the instrument 40 that is electrically conductive and able to outwardly transmit an electrical current to surrounding tissue/fluids.

FIGS. 3-6 schematically illustrate one embodiment of a stimulator 40 that may be used, for example, to access and electrically stimulate a nerve root that is compressed within a foramen of the spine (i.e., either the vertebral foramen that contains the spinal column, or the neural/intervertebral foramen where the nerve exits the spine). This stimulator 40 is particularly configured to gain direct access to the nerve root within the foramen via its specialized geometry, which is capable of extending around a portion of the spinal lamina either from an upper (superior) or lower (inferior) direction.

As generally shown, the stimulator 40 includes an elongate body 70, a handle 72 and/or handle connector 74 at a proximal end portion 76 of the body 70, and a stimulator tip 78 at a distal end portion 80 of the body 70. While the handle connector 74 and stimulator tip 78 may be electrically conductive and in electrical communication with each other, the exterior surface of the body 70 between the handle connector 74 and the stimulator tip 78 may be non-conductive. For example in one embodiment, the elongate body 70 may be substantially formed from a stainless steel material such as a 304, 316 or 316L type stainless steel alloy. As generally shown in the cross-sectional view provided in FIG. 4, surrounding/enveloping the stainless steel core 82 may be a layer of an electrically insulating material 84 that extends between the stimulator tip 78 and the handle connector 74. In some embodiments, this electrically insulating material 84 may comprise an oxide layer (e.g., such as may be present through an anodizing process), a polymer, a glass, or a ceramic material. In one embodiment, the insulating material 84 may comprise a deposited parylene coating. In other embodiments, the insulating material 84 may comprise a polymer such as, and without limitation, a polyvinylidene fluoride (PVDF), a polyether block amide (PEBA), a high-density polyethylene (HDPE), a cross-linked acrylated olefin, a polytetrafluoroethylene (PTFE), a fluorinated ethylene propylene (FEP), or a polyethylene terephthalate (PET).

Referring again to FIG. 3, to provide increased feel and tactile response through nerve-dense regions and around bony anatomy (which may not be directly visible due to such anatomy being on an internal side of the spinal lamina) at least a portion of the body 70 (and specifically the metallic core 82 of the body 70) may have a tapered cross-sectional profile that provides greater flexibility to the instrument at or near the distal end portion 80. Such a tapered profile may transition, for example from a maximum body diameter D1 of about 1.8 mm to about 2.2 mm (or about 1.9 mm to about 2.1 mm, or even about 2.0 mm) to a minimum body diameter D2 of about 0.7 mm to about 0.9 mm (or about 0.75 mm to about 0.85 mm, or even about 0.8 mm). In one configuration, the taper may be a constant taper that results in at least a 50% reduction in body diameter over a length of at least about 75 mm.

FIGS. 5-6 present an enlarged image of the stimulator tip 78 and distal end portion 80 of the body 70. As shown, in this embodiment, the stimulator tip 78 has narrow thickness T that is designed to more easily access tight spaces and a comparatively wider width W to ensure optimal electrical contact with the nerve. In some embodiments, the thickness T may be between about 0.4 mm and about 0.8 mm, (or between about 0.4 mm and about 0.6 mm, or even about 0.5 mm). In one embodiment, the tip 78 may have a width to thickness ratio of between about 3.5:1 and about 4.5:1, and a total stimulated surface area of between about 10 mm$^2$ and about 20 mm$^2$.

As best shown in FIGS. 3 and 5, the stimulator tip 78 and distal end portion 80 of the elongate body 70 may have a unique bend geometry that enables the electrically conductive tip to reach around the lamina and access a nerve within a foramen. More specifically, the stimulator tip 78 may be pitched at an angle A1 of between about 30 and about 80 degrees (or between about 40 and about 60 degrees, or even about 45 degrees) relative to a central axis CA of the body 70 (i.e., where the stimulator tip 78 is pitched in a tangential direction that is parallel to the thickness).

In some embodiments, to provide an adequate bend angle while also minimizing the required size of the working corridor used to access the spine, the distal end portion may include a compound bend such as shown in FIGS. 7-8. In this embodiment, the stimulator tip 78 may be joined with the body 70 via a neck portion 86 that is pitched at an angle A2 of between about 10 and about 25 degrees (or between about 12 and about 17 degrees, or even about 15 degrees) relative to a center axis CA of the body, while the stimulator tip 78 is then bent in the same plane as this "neck bend" to form an angle A3 between the stimulator tip 78 and the neck 86 of between about 100 and about 140 degrees (or between about 115 and about 125 degrees, or even about 120 degrees).

General Operation

During a surgical procedure, the user/surgeon may selectively administer the stimulus to intracorporeal tissue within the treatment area 12 (such as shown in FIG. 1) via the stimulator 40 to identify the presence of one or more nerve bundles or fibers or to test the function of a previously identified nerve. In some embodiments, the user/surgeon may administer the stimulus via the electrode 48 on the stimulator 40, for example, upon depressing a button or foot pedal 44 type input device or by tapping a soft-key on the user input display. The electrical stimulus 42 may, for example, be a periodic stimulus that includes a plurality of sequential discrete pulses (e.g., a step pulse) provided at a frequency of less than about 20 Hz, or between about 2 Hz and about 16 Hz. Each pulse may have a pulse width within the range of about 50 μs to about 400 μs. In other examples, each discrete pulse may have a pulse width within the range of about 50 μs to about 200 μs, or within the range of about 75 μs to about 125 μs. Additionally, in some embodiments, the current amplitude of each pulse may be independently controllable.

If a nerve extends within a predetermined distance of the electrode 48, the electrical stimulus 42 may cause the nerve to depolarize, resulting in a mechanical twitch of a muscle that is innervated by the nerve (i.e., an artificially-induced mechanical muscle response). As noted above, each NMS 34 may be specially configured to monitor a local mechanical movement of an adjacent muscle group of the subject 14. In response to this sensed movement, each respective mechanical sensor 50 may generate a mechanomyography (MMG) output signal 52 that corresponds to the sensed mechanical movement, force, and/or response of the adjacent muscle. The MMG output signal 52 may be either a digital or analog signal, and the NMS 34 may further include any communication circuitry or local processing circuitry that may be required to transmit the MMG output signal 52 (or a suitable representation thereof) to the host processor 38 via a wired or wireless communications. In some embodiments, the NMS 34 may further include a local alert capability, such as a lighting module or audible alert module that may operate at the direction of the local processing circuitry or local processor 38 to provide a corresponding visual or audible alert upon the detection of an event.

Detection Algorithm

As noted above, the system 10 may include resident software, firmware, or embedded processing routines that are operative to analyze the output from the neuromuscular sensors 34 in an effort to identify muscle responses that were induced by an electrical stimulus 42 applied via the stimulator 40 (i.e., an induced response). More specifically, these techniques/algorithms may attempt to establish with a high degree of confidence, that a detected muscle movement is the result of a nerve being artificially depolarized (i.e., via a stimulus administered by the stimulator probe) and that the detected motion is not simply a subject-intended muscle movement, an environmentally caused movement (e.g., bumping the operating table), or an artifact of another aspect of the procedure (e.g., sequential compression devices or cautery). In varying embodiments, the detection techniques/ algorithms may be performed in the analog/time domain, the digital/frequency domain, and/or may employ one or more wavelet analyses in an effort to promptly and accurately characterize any sensed motion. Additional techniques such as response gating, stimulus frequency modulation, artificial intelligence/structured machine learning, and/or ensemble approaches may also be used to make this detection more robust and/or provide a greater degree of confidence in the detection. While different detection techniques may each prove to be sufficiently effective in making this characterization, in many instances, however, detection confidence and detection speed/time are in conflict. The following will summarize analog/time domain detection techniques, digital/frequency detection techniques, and then go into further detail on wavelet-style analyses that have been found to generate more rapid responses for comparable levels of accuracy and at higher degrees of confidence.

Analog/Time Domain Event Detection

In some embodiments, the signal processing algorithms used to recognize an induced response may involve one or more analog detection techniques such as described, for example, in U.S. Pat. No. 8,343,065, issued on Jan. 1, 2013 (the '065 Patent), which is incorporated by reference in its entirety. In the analog techniques, the processor may examine one or more aspects of the MMG output signal 52 in an analog/time domain to determine if the sensed response includes signal attributes that are indicative of a response of the muscle to the stimulus. These analog aspects may include, for example, the time derivative of acceleration or the maximum amplitude of the M-wave/initial response being above a predetermined threshold. While these signal traits often have a high degree of sensitivity, they often deliver a significant number of false positives if viewed in isolation (i.e., a single spike in the waveform could just as easily be caused by a sharp bump of the operating table). As such, to provide a robust determination, multiple consecutive events need to be detected to make a final characterization. That said, in many instances ample muscle settling time must be provided between adjacent events to ensure that sequential muscle contractions do not overlap to introduce constructive or destructive signal interference in the waveform parameters, which are often dependent on absolute magnitudes or rates of change. The requirement for muscle settling time could limit the stimulation frequency to less than about 4 Hz, or even 2 Hz or less.

Digital/Frequency Domain

In a digital context, such as described in US 2015/ 0051506, filed on Aug. 13, 2013 (the '506 Application), which is incorporated by reference in its entirety, the processor may convert the analog waveform into the frequency domain (e.g., via a discrete fourier transform, or fast fourier transform) and then compare the frequency characteristics of the MMG output signal with the known frequency of the applied stimulation to determine whether the sensed muscle responses and/or "events" were induced by the applied stimulus. While this is a more robust form of detection than simply searching for discrete analog signal characteristics, the fourier transform necessarily requires a certain amount of accumulated data to perform the spectral decomposition. Thus, any performed analysis is necessarily occurring on buffered data and thus is delayed.

Wavelet Analysis

As a third potential manner of detecting artificially induced muscle responses, the system may include software or firmware that performs a wavelet similarity analysis on the incoming signals. The use of wavelet signal analyses presents an improvement over the frequency-domain detection techniques as it operates on real-time data as it is received without the need to convert to the frequency domain via an FFT. Likewise, it provides a more robust characterization than simply examining discrete signal parameters (e.g., magnitude or rate of change) in isolation.

In a wavelet analysis, one or more analog wave patterns may be pre-selected as being reference "mother wavelets" that bare a resemblance to a smoothed MMG event. A filtered analog waveform in the MMG output signal 52 may then be compared, in real time, to each mother wavelet to determine a degree of similarity between the two. If the presence of the mother wavelet is found within the analog signal, then the system may infer that an artificially induced muscular event has occurred. This is a more robust analysis than the analog method described above largely because it considers the entire wave shape rather than instantaneous parameters.

Because the responsiveness of each subject's muscles (and/or muscle groups) may have different dynamic properties, in some embodiments, the system 10 may also search for the presence of different time-scaled variants of the mother wavelet within the analog signal. These variants are generally referred to as "daughter wavelets," and are similar to the mother wavelet except in how compressed or stretched the wave is on the time-axis.

To perform this analysis, the system 10 may first derive a plurality of "daughter wavelets" from each mother wavelet, where the daughter wavelets are each time-scaled versions of their respective mother wavelet. When analyzing an incoming wave, the examined wave may be continuously passed across each daughter wavelet to determine a respective degree of similarity between the incoming signal and each daughter wavelet (i.e., the degree of similarity being expressed in the form of a "convolution coefficient"). The convolution coefficient for each daughter wavelet may then vary with time as the examined wave passes across the daughter wavelet. This analysis may be performed, for example, using a continuous wavelet transform or discrete wavelet transform and may output a 2d matrix 100 of convolution coefficients such as represented via the heat map in FIG. 9. In this figure, the convolution coefficient may be continuously computed for each scaled daughter wave (represented across the Y/Scale axis 102) and may be output continuously over time (represented on the X/Time axis 104). It should be appreciated that other wavelet-based analysis techniques exist (most commonly in the field of digital image compression) and may be used in combination with or instead of continuous or discrete wavelet transforms for the purposes described herein.

Figure 9:
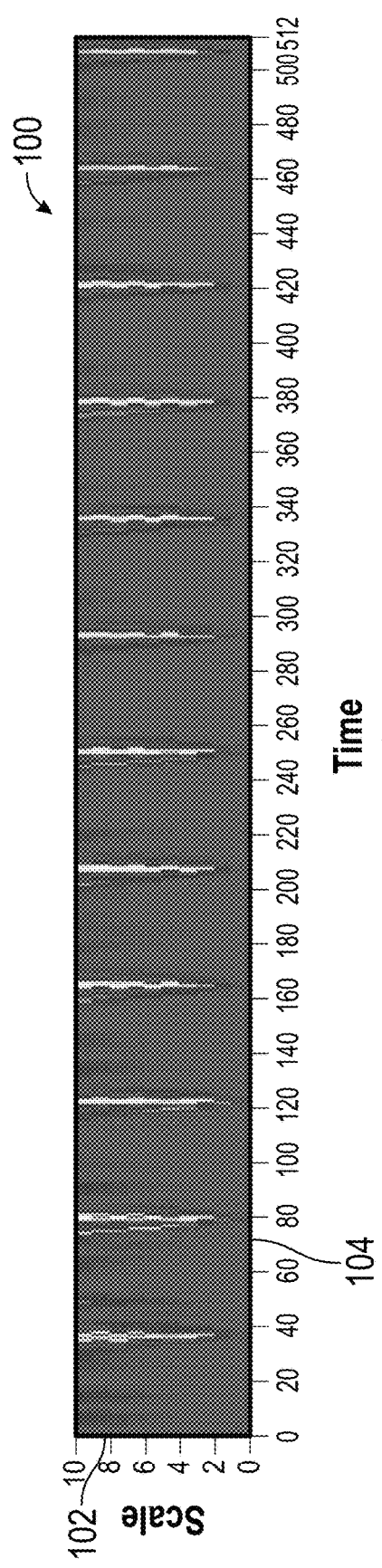
FIG. 9 is a schematic heat map illustrating the magnitude of a convolution coefficient computed for a plurality of different scaled waves (y-axis) across a plurality of different time steps (x-axis).
Figure 10:
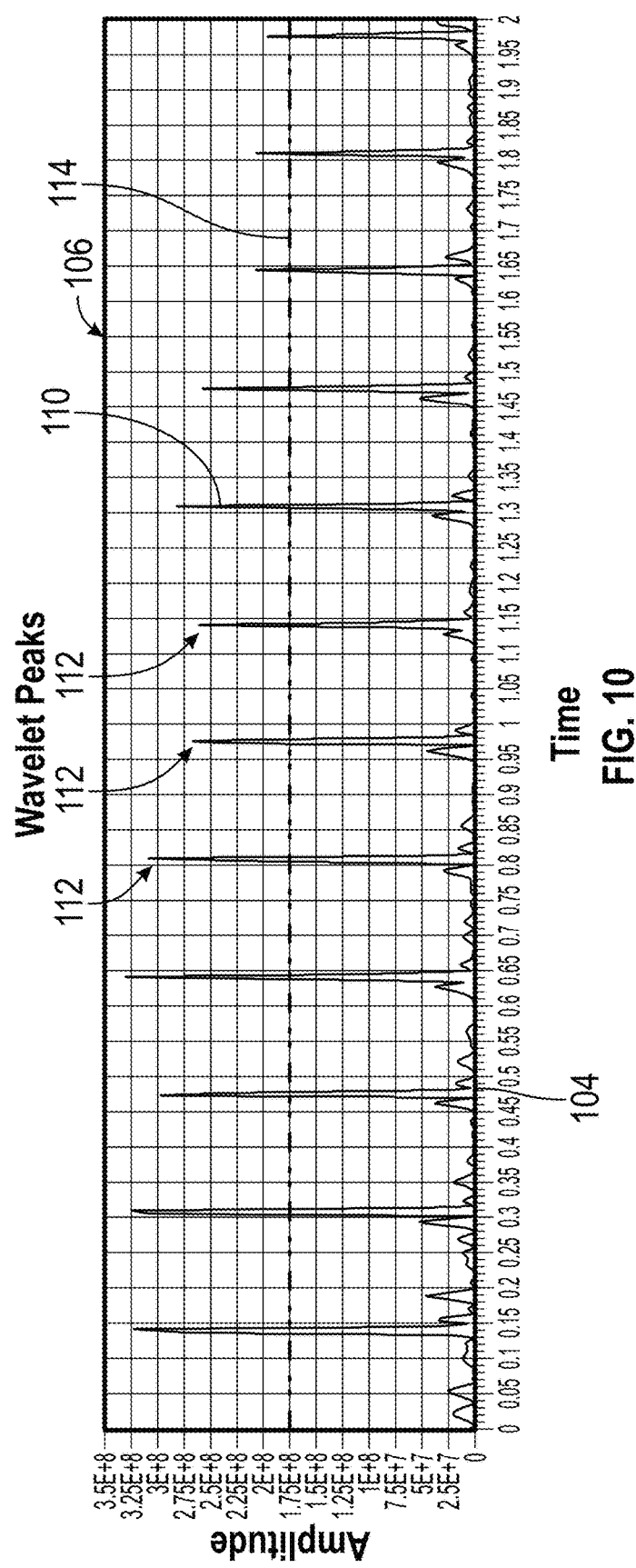
FIG. 10 is a schematic graph of a net convolution coefficient as a function of time, and formed by condensing the heat map of FIG. 9.

The heat map of FIG. 9 may then be consolidated into a more manageable 1-dimensional array 106 by summing the convolution coefficients of each daughter wave across the range of scales into a single net-convolution coefficient 110 (NCC 110) at each timestep, such as generally illustrated in FIG. 10. In some embodiments, each respective convolution coefficient at a time step may be squared prior to summing to ensure that the collection exclusively contains positive values. This is done so that regardless of the orientation of the input signal (whether in phase or out of phase with the wavelet), the output data is always collected as a positive contribution. This resulting 1-dimensional NCC 110 can then provide an indication of the likely temporal locations of the wavelet-like signal within the examined wave in real-time (i.e., with each peak corresponding to a candidate induced neuromuscular event).

As further illustrated in FIG. 10, the NCC may have distinct peaks 112 or spikes in magnitude that may be identified via the processor using a peak finding algorithm. Such a peak finding algorithm may examine the signal for points above a given threshold 114 (typically defined as a percentage of a maximum signal value) that have lower magnitude data points before and after in time. The processor may then process the data from the peak finder by determining whether adjacently identified peaks 112 occur at an expected periodicity. More specifically, in one configuration, the stimulating signal may be administered at a known frequency or periodicity. As used herein, the term periodicity is intended to refer to the spacing in time (i.e., "period") between adjacent peaks and is the inverse of the term "frequency." When examining the temporal identification of the peaks 112 in the NCC 110, the processor may determine a periodicity of the peaks 112 (i.e., by computing the time between adjacent peaks 112), and then compare this to the known periodicity of the stimulus. If the stimulus periodicity and NCC peak periodicity are similar (i.e., within a predefined error tolerance), then the system may conclude that the stimulus 42 is inducing the neuromuscular motion detected by the sensor.

Similar to the analog and frequency techniques described above, requiring an increased number of recorded muscle events/NCC peaks 112 prior to providing an alert would result in improved noise rejection and accuracy, while requiring fewer recorded muscle events/NCC peaks 112 prior to an alert, thus resulting in a faster alert time. In this manner, the wavelet detection techniques provides an ability for an early warning indication upon recognizing only two peaks in the NCC, while it may then provide a more confident alert as subsequent peaks are detected at the known periodicity.

Response Gating

Any of the above-described techniques may be made more robust by further considering only events or muscle activity that occurs within an expected response window following the administration/delivery of the stimulus. Conversely, responses that are "detected" outside of this response window may be aggressively filtered/attenuated or even ignored as not being the result of an applied stimulus (i.e., since no stimulus was administered, it's unlikely that any detected motion was stimulus-induced). In one embodiment, this filtering technique may simply include examining MMG signals for induced muscle response only when the stimulus is being actively applied and effectively turning off detection when the stimulus is not being administered.

In still other embodiments, because the neuromuscular sensors may continue to monitor throughout the duration of the procedure, signal content detected when the stimulus is off may then be used to filter the signal content while the stimulus is being administered. In doing so, background noise may be dynamically detected and filtered out to better isolate portions of the signal that may be representative of an artificially induced muscle response. For example, if there is a repeating 0.5 Hz wave that is detected by the neuromuscular sensor both inside and outside of the expected response window, a signal filter may be trained to remove this signal component from the MMG output signal prior to performing any analysis.

Error Rejection Via Variable Frequency Stimulation

During a surgical procedure, various equipment and interventional processes may act on the patient at various periodic frequencies (e.g., sequential compression devices). In some embodiments, the stimulation frequency may simply be selected to avoid any interference with known intervention frequencies that exist in common practice. In other embodiments, to provide even greater error rejection, the system may stimulate tissue via the probe at a variable stimulation frequency (i.e., a variable periodicity such that the time period between a first and a second provided electrical stimulus is not equal to the time period between the second and a third provided electrical stimulus). This technique may be most easily used in conjunction with a wavelet analysis, where, as shown in FIG. 10, the net-convolution coefficient 110 may generate peaks 112 that would have a varying peak-to-peak period that should directly correspond to the varying period of the administered electrical current.

This variable stim-frequency technique may be particularly applicable to a wavelet detection algorithm because the wavelet algorithm operates in real time on the received signal. In one configuration, the stimulation frequency may be continuously variable such that any two adjacent stim-to-stim periods may be different in length. Such a continuously variable stim-frequency technique is more difficult to implement if using a frequency-domain detection algorithm because the FFT used to decompose the analog signal into the frequency domain requires at least three or four cycles of data before it can provide a reliable frequency decomposition. If the frequency were to be continuously changing, then the FFT may identify a broader range of signal content that may be more difficult to properly characterize.

Dynamic Confidence Determination

It must be noted that each of the above-described detection techniques can yield statistically accurate detection results if provided enough time/data. For example, in an analog context, if 10 or more MMG events were detected in a consecutive sequence, where each event was identified as having a time derivative of acceleration value above a threshold, there is an extremely high likelihood that these 10 sequential events were caused by a corresponding 10 pulses of a stimulation current. Conversely, if only a single event were considered prior to making a determination, there is a much greater likelihood that this candidate "event" could be a false positive, which may have been caused simply by the operating table being bumped with a sufficient force. To this end, requiring more candidate events to confirm an alerted event may provide greater statistical accuracy/confidence in the determination, however it would also require a greater amount of time to reach that determination. This is because each "event" is a discrete contraction of the muscle that is induced by a separate electrical stimulus provided over time.

Figure 11:
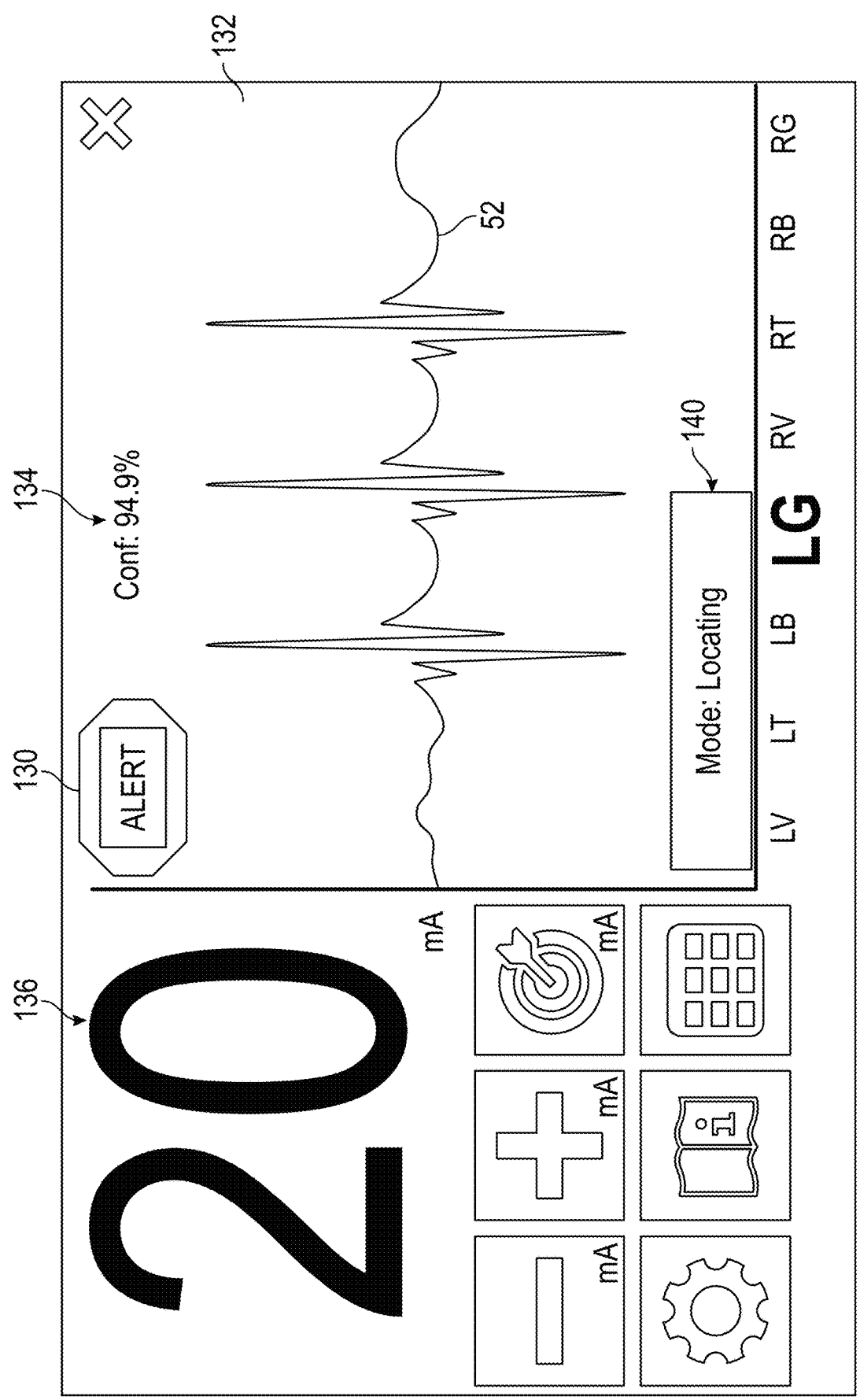
FIG. 11 is a schematic display screen for a neural monitoring system, such as shown in FIG. 1, with the display screen indicating that the system is in a nerve locating mode, though has high confidence that a nerve has been detected via a 20 mA stimulation current.

In view of the tradeoff between speed and confidence, in one configuration, the processor 28 may be configured to indicate or provide an alert 130 if a possible MMG event is detected, such as shown in the display screen 132 in FIG. 11, while also providing an indication of a statistical confidence 134 that the event is, in fact, a stimulus-induced muscle response. As further illustrated via the display screen 132 in FIG. 11, the processor 28 is further configured to provide an indication 136 of the magnitude of the electrical current administered via the electrode 48, as well as a raw or filtered analog trace of the MMG output signal 52. For example, referring to the wavelet discussion, above, if a single peak 112 is detected in the computed net-convolution coefficient 110, the system may provide an indication that an event is detected, however, it may also indicate that this detection has a comparatively low level of confidence because it is a singular event and therefore there is no peak-to-peak period yet. Upon detection of second consecutive event, the indication of the induced muscle response (e.g., an alert to a user) may persist, though the provided degree of confidence may increase. This is because now two candidate events have been detected, and further because now there is a peak-to-peak period that can be compared to the stimulation period. Upon detection of, for example, a third or fourth consecutive peak, the indicated degree of confidence may increase further (both because detecting three or four events provides more confidence than, for example, two or three events, but also because there is additional period-data, and at four cycles of data, the FFT may be more accurately computed and the output of the FFT may serve to further confirm the output of the wavelet analysis). As such, with more identified candidate events and elapsed time, the system has more and more data from which to make a more confident determination.

As demonstrated from this example, the processor may utilize different detection techniques in combination and/or may utilize varying detection criteria for any given technique to provide an overall confidence determination. If represented quantitatively, such as shown in FIG. 11, a statistical measure of confidence 134 may be a function to the sensitivity, specificity, positive predictive value (PPV), and/or negative predictive value (NPV) of the event determination based on the amount and nature of the information that has been received. In a non-limiting example, the statistical confidence reading may be the root-mean-squared (RMS) of the empirically determined PPV and NPV for the detection technique when trained against known data. As more data is received, this confidence determination may be refined upward (using new event info that supports the determination) or downward (based on identified signal parameters that are in conflict with a true event). In one embodiment, the confidence determination may be visualized on the display as a single column bar chart, a gauge, a dial, or any other qualitative or quantitative indication of the relative degree of confidence in the predictive value of the alert 130.

Providing a early indication of a possible event, along with a statistical indication of confidence in that determination may enable a faster time to detection and ultimately provide the surgeon with increased understanding and trust in the alert. While in some instances, detection speed may simply be a matter of convenience, in other instances it can directly impact usability and/or system dynamics. For example, if the system is serving as an input to a robotic system, an early indication of the presence of a nerve (even if associated with a low statistical confidence) may enable the control dynamics to more rapidly begin implementing prophylactic measures to slow or halt the robot's motion.

Confidence Using Wavelet Techniques

In one embodiment, the processor 28 of the neural monitoring system 10 may alert a user to the occurrence (or lack thereof) of an artificially induced neuromuscular response if one or more peaks 112 are identified in a net-convolution coefficient 110 (NCC), such as described above. Using an understanding of the system's capabilities via empirical data, the system may also be able to compute and output an indication of the confidence 134 of the alert 130 based on the number and periodicity of the identified NCC peaks 112.

To demonstrate this confidence determination, the data in the following table was obtained via controlled bench testing using a wavelet-style analysis and a 16 Hz stimulation signal. It must be noted that this data is illustrative based on preliminary testing and should not be relied upon as demonstrating any capabilities of a commercially available system or as the basis for medical decision making. This data demonstrates that a greater amount of confirmatory information serves to increase the positive predictive value (i.e., more data reduces the incidence of false positives), though that the system (in this test) is not prone to false negatives.

|  | 2 peaks | 3 peaks | 4 peaks |
| --- | --- | --- | --- |
| Sensitivity | 100% | 100% | 100% |
| Specificity | 44.2% | 88.4% | 99.6% |
| PPV | 64.2% | 89.6% | 99.6% |
| NPV | 100% | 100% | 100% |
| RMS (PPV, NPV) | 84.0% | 94.9% | 99.8% |

When using a wavelet analysis, however the NCC 110 is being computed in real-time (or near-real time), and peaks 112 are identified on a rolling basis. While it is clear that a 4-peak detection provides the maximum confidence and highest rate of true positives, every identification of 4 peaks necessarily begins as the observation of two peaks, followed by the observation of three peaks—thus confidence in the alert grows as successive peaks are observed. In this example, with an indication of the alert, the system may also indicate the determined confidence (e.g., PPV or RMS(PPV, NPV)) to the user.

Use Cases

Nerve Detection/Avoidance—Exploratory

In a first embodiment, the present system may be used in an exploratory or nerve-locating manner to detect the presence of nerves within an intracorporeal portion of a subject. Such a use may, for example, include making a lateral-access approach to the spine prior to dilating and/or retracting tissue. In such a use, rapid detection time may aid a surgeon in more fluidly navigating this intracorporeal space while receiving continual updates on the existence of nerves in the local area. Conversely, it may avoid a situation where the surgeon must advance a tool/probe, and then wait for the system to register a response before knowing whether it is safe to advance further.

In one embodiment, during such an exploratory mode of operation, the system may transmit an electrical stimulus via an electrode 48 provided on a distal end portion of an elongate instrument/probe 40 as the probe navigates the intracorporeal treatment area. In one configuration, for this free-space type of detection, the current of the stimulus may be between about 15 mA and about 25 mA, which should be a large enough current to depolarize any nerve within about 15-20 mm of the electrode. Using a wavelet detection approach, together with a dynamic confidence reading, the system may provide an indication of a muscle event 130 after only a single peak is recognized in the net-convolution coefficient. As more data is received, including a second peak, a third peak, a fourth peak, etc. the displayed confidence 134 of the event detection may increase on the display (e.g., numerically and/or graphically via charts). Such a confidence indication may inform the surgeon how likely it is that the alert is a true positive (i.e., that the alert is indicative of an artificially induced muscle response, and not simply a false positive). The provided confidence indication 134 may be further associated with color changes on the display, or changes in the tone of audible alerts that are played. Further, in the display screen, the system may indicate that the system is in a "locating" mode (at 140) which may broadly inform the surgeon that the system is operating simply to detect whether the stimulator 40 is approaching a previously unidentified nerve.

In a robotic surgery context, this low-confidence initial detection may prove very useful to the control systems, which must account for system dynamics in tool movement. Thus, in one configuration, even a low confidence detected event may impose limits on the robot as far as maximum probe tip travel speed, limits on angular movement, or limits on tool actuation.

Nerve Detection/Avoidance—Threshold Determination

Figure 12:
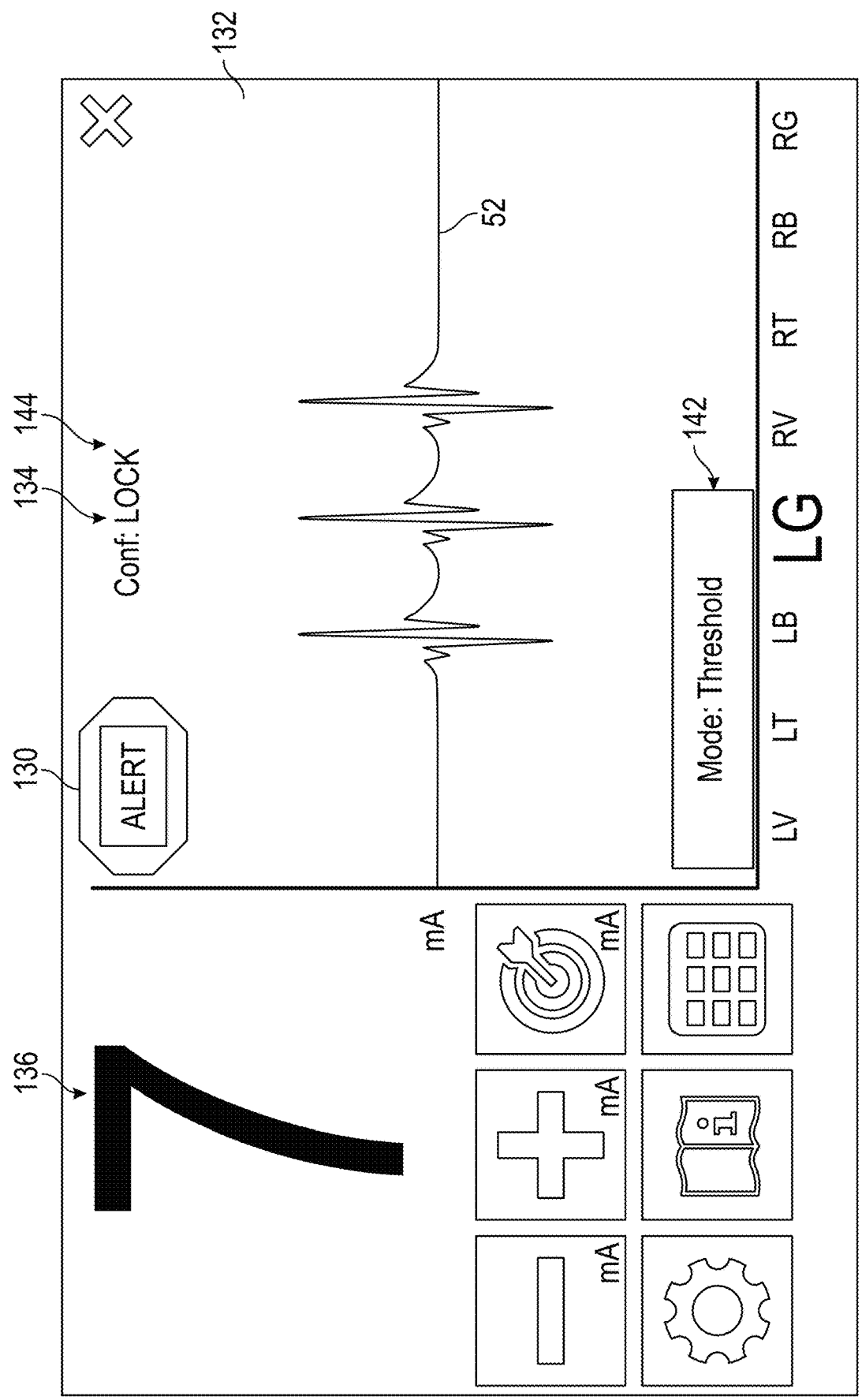
FIG. 12 is a schematic display screen for a neural monitoring system, such as shown in FIG. 1, with the display screen indicating that the system is in a threshold determining mode though has achieved a high-confidence "lock."

Once a neuromuscular response is detected with sufficient confidence (e.g., four successive peaks observed in the NCC 110), the system may then attempt to determine the minimum current that is required to induce a perceivable muscle response. This value has some clinical relevance as it is strongly correlated with the distance between the electrode and the nerve. During this threshold determination, the system may utilize a "confidence lock" feature to effectively lock on to a repeating muscle response and allow the magnitude of the stim current to vary from pulse-to-pulse. In some embodiments, when attempting to determine the minimum depolarization current for an identified nerve, the system may indicate, via the display 132, that the mode of operation is now threshold-finding 142 and may further provide an indication that the confidence is in a high confidence "lock" state 144, such as illustrated in FIG. 12. Once in this locked state, the processor 28 may disregard 1-pulse dropouts in the muscle response signal from affecting the detection confidence—provided those drop-outs coincide with a reduction in stim current (suggesting the stim current may have fallen below a nerve-depolarization threshold) and/or if they can be remedied by an immediate increase in stimulation current.

As an example of this technique, a surgeon may make an approach with a stimulated probe toward the spine with the system in the nerve-locating mode (as indicated at 140 in FIG. 11). Once a neuromuscular response is detected with sufficient confidence, the processor 28 may transition to a threshold-determining mode (at 142 in FIG. 12) and begin ramping down the magnitude of the current until it can be observed that a particular stimulus pulse fails to result in an observed or threshold peak 112 in the NCC 110. Due to the decreasing magnitude of the stimulus current, the processor 28 may assume that the lack of the response is more attributable to an insufficient current to depolarize the nerve, and not because the nerve (which confidently existed a moment ago), suddenly disappeared (or significantly moved relative to the probe). To confirm this assumption, the processor 28 may then increase the current magnitude to a prior (or simply a higher) level and examine if the peak 112 returns. If it does, the system may remain in the confidence lock state, while further concluding that the depolarization threshold current lies between the prior two current levels, which may then be indicated to the surgeon.

If the probe continues advancing toward (or away) the nerve, the system may attempt to follow this depolarization threshold by modulating the current in a similar scheme while maintaining the confidence lock so long as any drop out can be remedied by an increase in current. If the current magnitude returns to its original exploratory level (e.g., 15 mA to 25 mA), and multiple no-responses are observed, then the system may return back to a high confidence no-nerve state. Through this process, a decreasing depolarization threshold would indicate that the motion of the probe is bringing the electrode closer to the nerve, whereas an increasing depolarization threshold would indicate that the electrode is moving away from the nerve. By using the wavelet analysis technique in this manner, the processor may track the depolarization threshold on only a one pulse/cycle lag as opposed to, for example, an FFT approach that requires 3-4 cycles/pulses of data for each analysis.

Nerve Health Diagnostics

In one embodiment, present system may be used to determine the health, or change in health of a nerve. More specifically, as nerves become compressed within a neural foramen, they lose their ability to transmit a clean neurological impulse to the muscle that they innervate. Assuming that the nerve has not been permanently damaged through prolonged compression, decompressing the nerve by removing the stenosis or impinging tissue can result in an almost immediate improvement in nerve function. In this manner, the present system may be used to determine both the extent of a nerve compression, as well as to serve as an intraoperative diagnostic tool to identify the point at which the nerve is sufficiently decompressed (which may provide an indication to conclude the procedure).

To perform the nerve health diagnostics, it is preferable to directly stimulate the nerve or nerve root, via contact between the electrode and the nerve, both before and after the decompression to assess changes in the nerve/muscle response. To accomplish this direct stimulation, in one configuration, a stimulator probe such as shown in FIG. 3 or FIG. 7 may be inserted into the vertebral foramen above or below the posterior lamina and the electrode 48 may be brought into contact with the nerve (i.e., contacting the nerve on the anterior side of the lamina). The thin/flat geometry of the above-described stimulator tip provides a surgeon with the ability to make this direct contact even if an impingement or stenosis provides minimal space that would not accommodate more traditional (e.g., ball tip) probes without some degree of pre-decompression first.

Once in contact with the nerve, the system may attempt to determine the minimum amount of current that is required to sufficiently depolarize the nerve and induce a perceivable muscle response. In the case of healthy nerves, the minimum required current to induce a muscle response may be between about 1 mA and about 6 mA, or more preferably between about 1 mA and about 3 mA. Conversely, some compressed nerves may require between about 15 mA and about 30 mA to elicit the same threshold response. By testing the minimum required current before, during, and after the decompression, the surgeon may better understand the initial health and/or functionality of the nerve, and whether further decompression or exploratory efforts may be required to provide a successful outcome.

The present system may utilize various techniques to determine the minimum current in the shortest amount of time. For example, in one configuration, the system may linearly ramp the current up from 1 mA to a point where a muscle response is detected. In another configuration, the system may use algorithmic targeting techniques to identify the minimum required current in the fewest number of iterative steps. Such a targeting technique may involve identifying a total working current range and then testing a current value at the center of the working range. This test should result in one of the two created sub-ranges being bounded by a current value that does not induce a muscle response on the low end, and a current value that does induce a muscle response on the higher end of the sub-range (i.e., in binary terms, this sub range could be represented as a "0-1" range—as opposed to a "0-0" range where neither endpoint sees a muscle response or "1-1" range where both endpoints see a response). The system may then test at the center point of the identified 0-1 subrange to then identify a 0-1 sub-subrange within the previously identified 0-1 sub-range. This process may repeat until a suitable sub-range resolution is achieved that contains the actual threshold. If the initial starting range was 0-20 mA, then it would only take five tests to identify the minimum current threshold with sub-1 mA resolution (20/(25)=0.625 mA resolution).

While it is certainly possible to perform each test in this sequence of five tests to a full confidence (i.e., where each test requires a sequence of consecutive simulations/muscle responses), in some embodiments, the process may be further sped up using a wavelet approach that takes into account the confidence of the determination. For example, the first test (e.g., at 20 mA) may have a lower required confidence threshold to determine an event than the later tests.

Alternatively, the system may utilize a similar "confidence lock" scheme as described above to home in on the threshold while altering the current magnitude between each successive pulse (i.e., once a lock is established). For example, the system may begin at a high current (e.g., 20 mA) in an attempt to achieve a response and high-confidence lock. Once locked in this high-confidence mode via a plurality of successive responses having a periodicity that approximates or is about equal to a periodicity of the stimulus, then each successive test may only require a single stimulus pulse. If, by dropping the current, a response is not recorded, and then the current is increased on the next stimulus and the muscle response returns at the expected time, then the high confidence lock may be maintained. As an example, if the threshold for a high-confidence lock is three consecutive events occurring at a periodicity that is about equal to a periodicity of the stimulus, then the stim sequence to home in on a 6.5 mA threshold may proceed as set forth in the table below:

| Pulse No. | Current | NCC Peak Detected? | Comments |
|---|---|---|---|
| 1 | 20 mA | Yes | Establishes High |
| 2 | 20 mA | Yes | Confidence Lock |
| 3 | 20 mA | Yes | |
| 4 | 10 mA | Yes | Bounded Range: 0-10 mA |
| 5 | 5 mA | No | Bounded Range: 5-10 mA |
| 6 | 7.5 mA | Yes | Bounded Range: 5-7.5 mA Negates missed peak on pulse 5 |
| 7 | 6.125 mA | No | Bounded Range: 6.125-7.5 mA |
| 8 | 6.813 mA | Yes | Bounded Range: 6.125-6.813 mA (sub-1 mA accuracy) |

In this example, the first three 20 mA stim pulses are used to establish the high-confidence lock, and then the subsequent 5 pulses are each singular pulses, with the step up from 5.0 mA to 7.5 mA in pulse #6 and the step up from 6.125 mA to 6.813 mA in pulse #8 (and return of the NCC peak in each instance) negating any drop in confidence from the lack of response at 5.0 and 6.125 mA, respectively. If stimulated at an 8 Hz stim frequency, this total detection scheme would take 1 second—as compared with other detection techniques that may require 20 or more stim pulses, and multiple seconds of detection time, to arrive at the same detection resolution (potentially at even slower stim frequencies).

Multi-Stage Detection Approach

While the techniques described thus far offer robust capabilities for detecting artificially induced neuromuscular events, additional processing modalities can be employed to further enhance detection speed, accuracy and adaptability. As an example, a multi-stage analysis approach can be implemented that combines rapid pre-classification of potential events with a more rigorous waveform verification process. This approach not only improves underlying detection capabilities, but can also enable the integration of modern methods such as machine learning for heightened performance over time. In the multi-stage technique, candidate waveforms are first identified in the incoming sensor data based on signature analog or digital signal characteristics. These potential events are then passed to a classification module that compares sequential candidates to confirm they exhibit expected morphological similarities, reducing false positives. The modular architecture permits optimization and tuning of each stage independently, providing flexibility. Additional preprocessing or post-processing stages may also be incorporated to isolate signal components or further verify classified events. Furthermore, the waveform correlation analysis can be augmented using machine learning, where a model learns to recognize complex patterns that typify real neuromuscular responses. Continuous retraining can further adapt the model to changing signal characteristics or to a patient's unique physiology. When interfaced with the modular multi-stage workflow, machine learning can impart accurate and robust detection capabilities.

Figure 13:
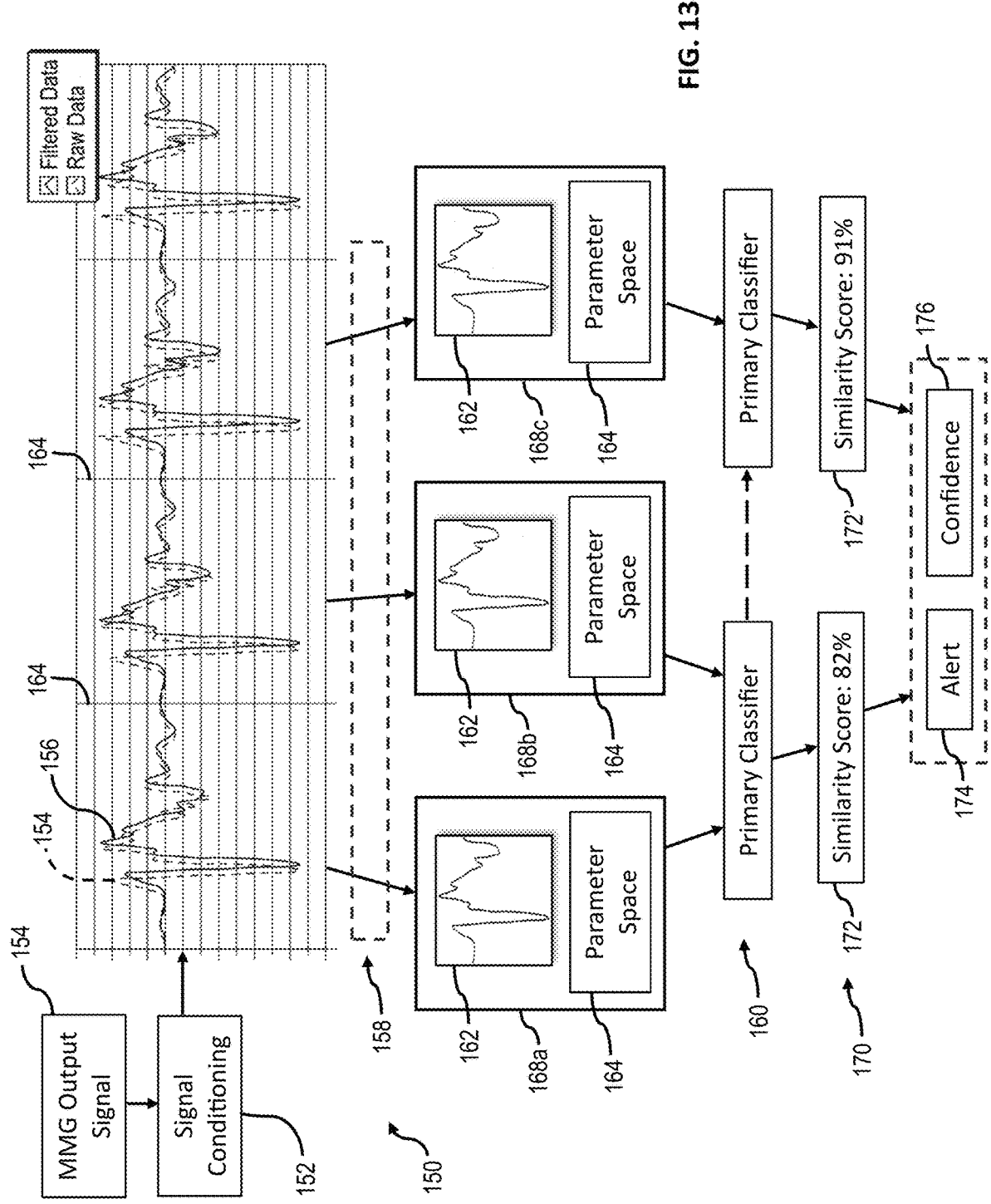
FIG. 13 is a schematic diagram of a multi-stage detection approach for detecting an artificially induced muscle response.

FIG. 13 schematically illustrates one embodiment of this multi-stage detection approach 150, which may begin at 152 by applying one or more signal conditioning filters to the MMG output signal 154 received from the NMS 34. These conditioning filters at 152 may include one or more low pass filters, high pass filters, bandpass filters, Butterworth filters, or other such similar analog or digital signal conditioning techniques to attenuate unwanted noise. The conditioning filters 152 may be applied digitally via the processor, or may be implemented using one or more passive or active electronic components apart from the processor. Following this initial low-level filtering, the processor may then pass the resultant waveform 156 through a pre-classification stage at 158 and then through a primary classification stage 160 as discussed further below.

Pre Classification Stage

Following any applied signal conditioning at 152, the resultant waveform 156 may be passed to the pre-classification stage at 158, where the waveform 156 may be examined to identify signal segments 162 that may be indicative of an artificially induced muscle response. These signal segments 162 may broadly be referred to as "candidate waveforms 162" and may include any analog signal wave that meets one or more predefined signal characteristics that are generally found within an induced muscle response. In some embodiments, these signal characteristics may include, for example, the time derivative of acceleration exceeding a threshold, the absolute power of the signal exceeding a threshold, a change in the power of the signal exceeding a threshold, peak signal amplitude exceeding a threshold, an elapsed amount of time/number of samples between a maximum and a minimum extrema of the wave, an identified peak in a convolution coefficient or net convolution coefficient (NCC) from a wavelet analysis, an elapsed amount of time from a reference point 164 to a maximum or minimum extrema of the wave, or an elapsed amount of time from a reference point 164 to the first zero-crossing after the reference point 164. In general, some or all of these signal characteristics may define the "parameter space 166" of the candidate waveform 162. If the time from a reference point 164 were used, in some embodiments, the system may define the reference point 164 as a function of the applied electrical stimulus. For example, the reference point 164 may be a point in the waveform 156 that is synchronized with the rising edge of a square wave pulse within the applied electrical stimulus.

In some embodiments, for every candidate waveform 162, the processor may store a representation of the candidate waveform 162 and/or some of all of the parameter space 166 of that waveform 162 in a buffered memory (i.e., records 168a, 168b, 168c—generically referenced herein as record 168). In some embodiments, the recorded representations of the candidate waveform 162 may include or otherwise may be a normalized and/or time-scaled variant of the original candidate waveform 162.

Primary Classification Stage

While it might be possible to flag every candidate waveform 162 as being the product of an electrically induced muscle depolarization, in reality, this would lead to a false positive rate that is beyond acceptable limits and would negatively affect the usability of the system. Therefore, a primary classification stage 160 may be employed to make the final determination of whether one or more candidate waveforms 162 are indicative of an artificially induced muscle response. In one configuration, this determination may occur by examining the similarity between any two or more sequential records 168/candidate waveforms 162.

In a very general sense, the primary classification stage 160 may operate on the theory that muscle responses induced by sequentially applied electrical stimuli should have generally similar response characteristics. Therefore, the primary classification stage may examine the analog candidate waveform 162 and/or associated parameter space 166 and make a comparison between immediately adjacent records 168 to determine a degree of similarity (generally at 170). In some embodiments, the degree of similarity 170 may be represented as a numeric similarity score 172. This numeric similarity score 172 may be a function of, for example, a similarity between the candidate waveforms 162 (e.g., Fréchet distance, mean absolute error, area between curves, etc.), and/or through one or more differences in the parameter space 166.

If the computed similarity score 172 is above a predetermined threshold, the processor may provide an alert 174 to the user that an induced muscle response has been detected. Furthermore, as shown in FIG. 13, the processor may output a confidence metric 176 which may be a function of the similarity score. In some embodiments, the confidence metric 176 may be the same as the similarity score 172. In other embodiments, the confidence metric 176 may be a probabilistic output based on the similarity score 172 and number of candidate waveforms that are sequentially detected. Such an alert 174 and/or confidence metric 176 may be used in any of the manners described above, including, but not limited to in an exploratory or nerve-locating manner to detect the presence of nerves, to determine the minimum current that is required to induce a perceivable muscle response, and/or to determine the health, or change in health of a nerve. Further, because only two waves are required to generate an alert (i.e., provided that the similarity score is above a predefined threshold), this multi-stage detection technique would provide similar detection speed benefits as the wavelet techniques described herein.

As additional candidate waveforms 162 are detected (e.g., record 168c), the processor may utilize the new insight to generate a refined similarity score 172', which may then be used further refine the output alert 174 and/or confidence metric 176 (i.e., for the purpose of confirming or rejecting an identification made through the first comparison). Conversely, if a period of time elapses without identification of a new candidate waveform 162, or else if one or more stimuli are applied and no candidate waveform is detected, then the classification stage may be reset. Alternatively, in some embodiments the confidence metric may decay toward zero as a function of elapsed time without new detected events. In such an embodiment, once the confidence metric falls below a predefined threshold, then the system my cease displaying the alert 174.

In some embodiments, the primary classification stage 160 of the multi-stage detection process could additionally leverage machine learning to further improve performance. Rather than relying on predefined similarity metrics, the waveform comparisons could be based on a machine learning model trained on labeled sample data. This would enable the model to assess similarity in a more complex, nonlinear fashion and identify intricate patterns between candidate waveforms that may be indicative of artificially induced neuromuscular responses. Moreover, continuous retraining of the model on newly acquired data during operation would allow the similarity assessments to dynamically adapt to the latest response patterns, progressively improving detection accuracy over time. The multi-stage architecture readily supports the integration of modern machine learning techniques to supersede the limitations of fixed algorithms and better handle evolving signal characteristics in long-term use cases.

More specific to embodiments utilizing machine learning, the primary classification stage may, for example, employ a supervised machine learning model trained to distinguish true neuromuscular response waveforms from false positives. The model could be trained on labeled example data containing both positive and negative instances of candidate waveforms. Such data may include: true positives (candidate waveforms confirmed as true responses based on timing alignment with applied electrical stimuli); Negative candidate waveforms (candidate waveforms occurring asynchronously with respect to stimulation timing); and negative noise (random noise signals as additional negative examples).

Within this supervised learning model, a variety of machine learning algorithms could be used, such as random forest classifiers or deep neural networks. The model may learn to recognize complex patterns and features within the multidimensional candidate waveform data that characterize true neuromuscular responses.

During a live procedure, new candidate waveforms would be fed to the trained model, which would output a similarity score reflecting the probability that the new waveform represents a true positive instance based on its learned recognition capabilities. A high probability from the model indicates the waveform is a likely real response. This probability figure may further be output to the user as a confidence metric to illustrate the certainty with which the alert is being provided.

In some embodiments, the model may be continuously retrained on new data from ongoing operations to adapt to changing equipment, sensors, or patient response characteristics, or unique patient physiology. In some embodiments, the model may further consider patient data received from an electronic medical record datafile. Such data may include, functional strength data, patient height and weight, patient body mass index or body fat composition, evidence of diabetes or neuropathy, age, prior neurological diagnostic testing, and the like. Advanced techniques like transfer learning could further allow the model to leverage learnings from past uses and patients when being retrained for new deployments, avoiding lost knowledge.

The modular design of the multi-stage detection approach readily accommodates the incorporation of additional analysis stages as needed to further improve performance. For example, a post-classification stage could be implemented to apply frequency domain techniques, such as a Fourier or wavelet transform, to the candidate waveforms that were classified as positive events. This additional verification using spectral analysis may further reduce false positives by confirming that the frequency content of the detected events matches the expected neuromuscular response profile. Furthermore, supplementary preprocessing stages could be added to isolate particular components of the sensor signal prior to detection and classification. Such preprocessing may encompass noise filtering or artifact removal to enhance the signal-to-noise ratio of the data and mitigate sources of false readings. These additional analysis stages can be integrated with the core multi-stage architecture in a straightforward manner to address the needs of different applications or operating environments.

The multi-stage detection approach can also be readily combined with complementary analysis techniques to further bolster performance. For instance, frequency domain features could be incorporated during the primary classification stage to augment the time-domain similarity scoring. Techniques such as the Fourier or wavelet transform could extract spectral characteristics of each candidate waveform, which could then be included in the similarity metric computations alongside temporal correlation analysis. This would enable similarity assessments based on both time-domain morphology and frequency content similarity. Additionally, ensemble approaches that integrate the outputs of the multi-stage analysis with other detection methods could be pursued to combine strengths while minimizing limitations. Such an ensemble technique would simply increase the system confidence in the alert as sufficient data is received to perform the various analyses. By fusing the probabilistic outputs using techniques such as weighted averaging or voting, the multi-stage technique could contribute its accuracy and speed to an ensemble model that offers improved overall event detection capabilities. Such combinations exemplify the flexibility of the modular multi-stage architecture for integration with existing strategies.

The presently disclosed multi-stage approach confers several advantages that improve overall performance. The initial pre-classification stage allows for rapid identification of potential neuromuscular events based on specific time-domain signal characteristics. This improves detection speed by isolating candidate waveforms early in the analysis. False positives are subsequently minimized by the classification stage, which verifies similarity between sequential candidate events. Overall, the multi-stage design combines the benefits of both time-domain and pattern recognition analysis. The modular architecture also permits each stage to utilize the optimal analysis techniques for its intended purpose, whether that involves applying time-domain thresholds during pre-classification or assessing waveform similarity in the classification stage. Further flexibility is conferred by the ability to tune each stage independently to optimize the accuracy, speed, and robustness of event detection based on the application.

Robotic System with Rapid Nerve Detection

Figure 14:
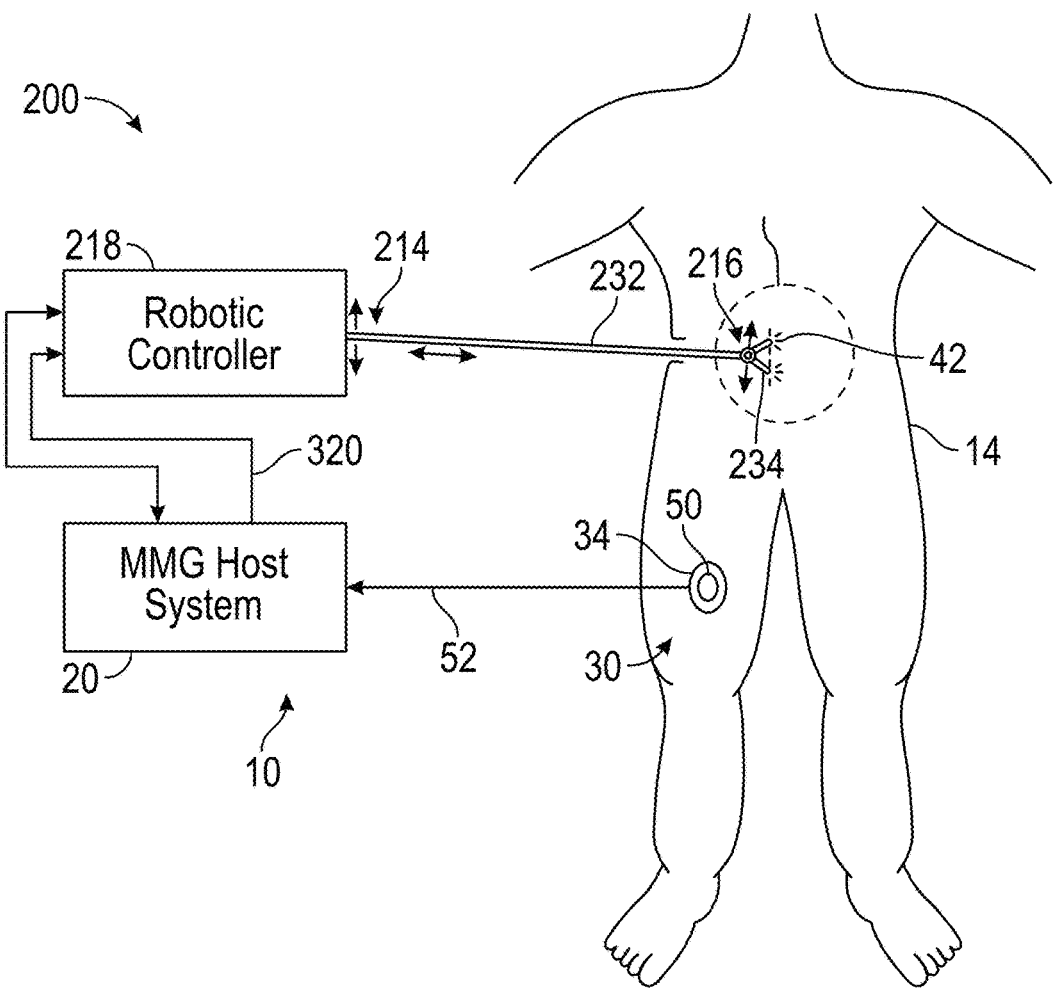
FIG. 14 is a schematic illustration of a robotic surgical system with mechanomyographic feedback being used in conjunction with a human subject.

FIG. 14 schematically illustrates a robotic surgical system 200 for performing a surgical procedure within the body of a subject 14. As illustrated, the robotic surgical system 200 includes an elongate surgical instrument 212 having a proximal end portion 214 and a distal end portion 216, a robotic controller 218 configured to control the motion of the distal end portion 216 of the surgical instrument 212, and a neural monitoring system 10 in communication with the robotic controller 218. As discussed above, the neural monitoring system 10 may include a sensing device 30 that includes at least one neuromuscular sensor (NMS) 34 that is coupled with the carrier material 32 and is operative to monitor a muscular response of the subject 14. each NMS 34 may comprise a mechanical sensor 50 that is operative to monitor the relative movement of the muscle that the NMS 34 is most closely coupled with.

During a surgical procedure, the surgical instrument 212 may extend through an opening in the body of the subject 14, with the distal end portion 216 disposed within the body of the subject 14, and the proximal end portion 214 disposed outside of the body of the subject 14. In one configuration, the surgical instrument 212 may generally be defined by a rigid elongate body 232, such that movement of the proximal end portion 214 of the instrument 212 may result in a predictable movement of the distal end portion 216 of the instrument 212.

The surgical instrument 212 may further include an end effector 234 disposed at the distal end portion 216. The end effector 234 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 234 may be configured to selectively rotate and/or articulate about the distal end portion 216 of the surgical instrument 212 to enable a greater range of motion/dexterity during a procedure.

In one embodiment, such as generally illustrated in FIG. 14, the end effector 234 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 232 of the instrument 212.

Figure 15:
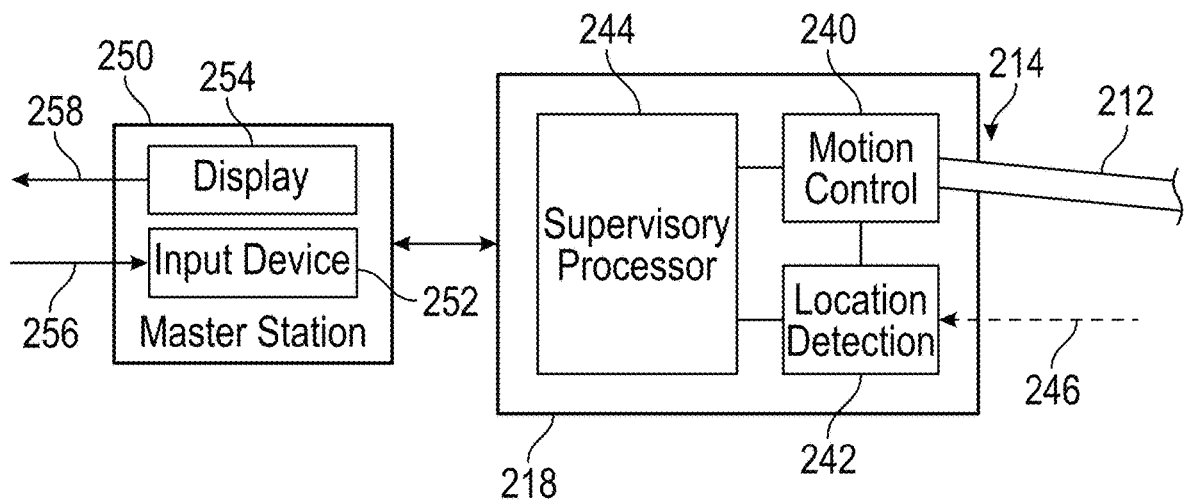
FIG. 15 is a schematic diagram of a robotic controller such as may be used with the robotic surgical system of FIG. 14.

The robotic controller 218 may be responsible for controllably performing a minimally invasive surgical procedure within the body of the subject 14 by controllably manipulating the proximal end 214 of the surgical instrument 212 in a manner that results in a controlled motion of the distal end portion 216. As generally illustrated in FIG. 15, in one configuration, the robotic controller 218 may include a motion controller 240, a location detection module 242 and a supervisory processor 244. The motion controller 240 may include a plurality of motors, linear actuators, or other such components that may be required to manipulate the proximal end 214 of the surgical instrument 212 in six or more degrees of freedom. (e.g., three degrees of translation, three degrees of rotation, and/or one or more degrees of actuation). Additionally, the motion controller 240 may include one or more processors or digital computers and/or power electronics that may be required to convert a received motion command into a physical actuation of a motor or actuator.

The location detection module 242 may include one or more digital computers or processing devices that may be configured to determine the position/motion of the distal end portion 216 of the surgical instrument 212, such as relative to one or more external reference frames. In one configuration, the location detection module 242 may monitor the behavior of the motion controller 240 to determine the motion of the distal end portion 216 using kinematic relationships of the surgical instrument 212. In another configuration, the location detection module 242 may receive a location signal 246 from an external, positioning system (not shown), which may resolve the position of the distal end portion 216 of the surgical instrument 212 using, for example, ultrasound energy, magnetic energy, or electromagnetic energy that may be propagated through the subject 14.

The supervisory processor 244 may be embodied as one or more digital computers or data processing devices, each having one or more microprocessors or central processing units (CPU), flash memory, random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 244 or readily accessible thereby may be stored in flash or other suitable tangible memory location and/or memory device, and automatically executed by associated hardware components of the processor 244 to provide the respective control functionality. In one embodiment, the supervisory processor 244 may provide the motion controller 240 with actuation commands in a closed loop manner using the positional feedback provided by the location detection module 242.

The supervisory processor 244 may perform any combination of feedforward, feedback, and/or predictive control schemes to accurately control the motion and/or actuation of the distal end portion 216 of the surgical instrument 212.

Additionally, the robotic controller 218 may be in communication with a master station 250 that includes a user input device 252 and a user feedback device such as a display 254. The user input device 252 may receive an input 256 from a user that corresponds to an intended movement of the distal end portion 216 of the surgical instrument 212. The master station 250 may then provide a motion command to the robotic controller 218 that corresponds to the received input 256. Similarly, the master station 250 may receive visual information 258 from the robotic controller and convey it to the user via the display 254.

While FIG. 15 provides one embodiment of a robotic controller 218, other embodiments, configurations, and or control schemes may similarly be used to manipulate the surgical instrument 212 in a manner that results in a controlled, and intended motion of the distal end portion 216. While the robotic controller 218 and surgical instrument 212 described above are generally of the kind used for robotic laparoscopy, such description is made for illustrative purposes and should not be limiting. Other minimally invasive surgical systems that employ a robotic controller 218 to control the motion of the distal end of an elongate surgical instrument may include, for example, robotic catheter systems and/or robotic endoscopic systems.

Referring again to FIG. 14, the robotic surgical system 200 includes a neural monitoring system 10 in communication with the robotic controller 218. The neural monitoring system 10 may provide the robotic controller 218 with an awareness of nerves that may be adjacent to the distal end portion 216 of the surgical instrument 212. In this manner, the robotic system 200 may avoid manipulating tissue (either through translational motion or actuation of an end effector 234) that may jeopardize neural integrity.

During a surgical procedure, the elongate surgical instrument 212 may emit a stimulus 42 within the intracorporeal treatment area 12 of the subject 14 similar to the simulator 40 described above. The stimulus 42 may be, for example, an electrical stimulus, though may alternatively be a thermal, chemical, ultrasonic, or infrared stimulus.

With continued reference to FIG. 14, if the neural monitoring system 10 detects an induced muscle response via the NMS 34, it may then provide a control signal 320 to the robotic controller 218. The control signal 320 may include an indication that an induced muscle response was detected. In some embodiments, this indication may include one or more of: a binary alert/signal (i.e., a nerve either is detected or it is not detected); an indication of the confidence of a detection (i.e., using one or more of the techniques described above), an indication of proximity between the distal end portion 216 of the surgical instrument 212 and a depolarized nerve, and/or an indication of a minimum current required to induced a muscle response.

Upon receipt of a control signal 320, the robotic controller 218 may artificially constrain the motion of the distal end portion 216 of the surgical instrument 212 to avoid inadvertent contact with a proximate nerve 340. For example, in one configuration, the robotic controller 218 may be configured to prevent all motion of the distal end portion 216 of the surgical instrument 212 in response to the received control signal 320. As such, if the distal end portion 216 was in motion, the received control signal 320 may cause the controller 218 to halt such motion and await a further command from the user. Additionally, the robotic controller 218 may be configured to limit or prevent actuation of an end effector 234 upon receipt of the control signal 320. Conversely, in certain therapeutic procedures, the robotic controller 218 may be configured to actuate the end effector 234 upon receipt of the control signal 320 (e.g., selectively deliver ablative energy to tissue proximate to the nerve).

Figure 16:
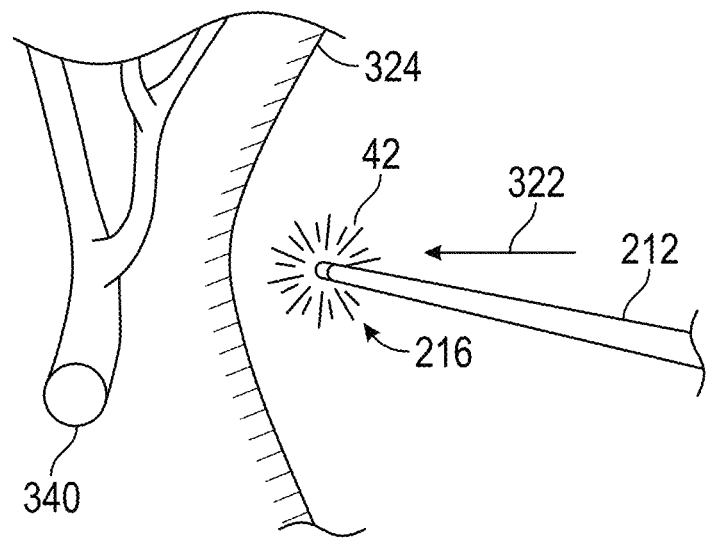
FIG. 16 is a schematic view of a distal end portion of an elongate surgical instrument moving with respect to a nerve of a subject.

In another configuration, such as schematically illustrated in FIG. 16, upon receipt of the control signal 320, the robotic controller may note the direction 322 of the motion of the surgical instrument 212, and may limit further instrument motion in that direction 322 (or directions with a component vector substantially aligned with the direction 322 of motion).

Figure 17:
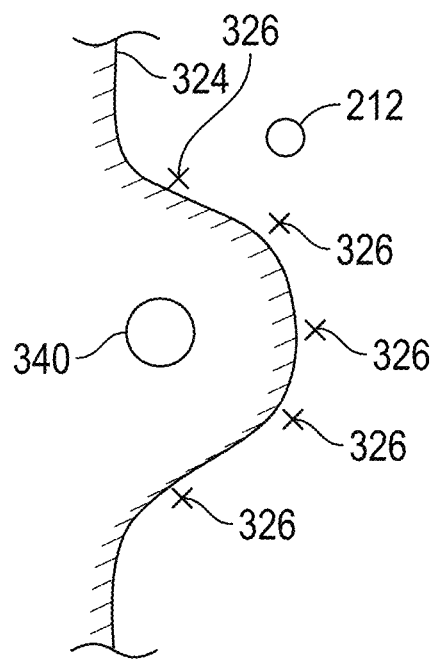
FIG. 17 is a schematic cross-sectional view of FIG. 16, with a virtual barrier being erected about the nerve.

In still another configuration, the robotic controller 218 may construct a virtual barrier 324 based on the direction of motion of the surgical instrument 212, and the location 326 of the instrument 212 when the control signal 320 was received. The virtual barrier 324 may be maintained in an associated memory of the robotic controller 18, and may limit the allowed range of motion of the surgical instrument 212, such that the surgical instrument 212 is artificially restricted from crossing the virtual barrier 324. As generally illustrated in FIG. 17, as the surgical instrument 212 moves, the virtual barrier 324 may be refined according to the receipt of successive control signals 320/locations 326.

Once a nerve is detected, the robotic controller 218 may be configured to vary the permitted speed of the distal end portion 216 of the surgical instrument 212 as a function of the indicated proximity between the real-time location of the instrument 212, the minimum current required to induced a muscular response, and/or the determined confidence of the detection. As such, the instrument 212 may be allowed to move more quickly and/or at a higher rate of speed when it is farther from the nerve. Similarly, by understanding the confidence of a detection, the robotic controller 218 may effectively have an early warning or advanced notice that a confirmed detection may be incoming. In this manner, maximum permitted tip speed may decrease as the confidence of the detection increases. Once a high confidence lock is established (e.g., 4 or more consecutive induced muscle responses have been detected), the maximum permitted tip speed may vary as a function of stimulus magnitude and/or the magnitude of the detected response. Similarly, if a induced muscle event is detected (i.e., even if it is a low confidence detection), the robotic controller 218 may limit or prevent the actuation of any end effector that may compromise nerve integrity until the alert is cleared. In some embodiments, the surgeon may be provided with the ability to override such a tool restriction, though not until the surgeon is fully alerted of the risk.

If the presence of a proximate nerve is detected (via an induced muscle response), and/or if an action is performed by the robotic controller 218 to adjust or limit the allowed motion of the surgical instrument 212, the robotic controller 218 may likewise transmit an alert (i.e., a visual alert or an auditory alert) to the user via the master station 250.

Using the system described above, robotic, minimally invasive surgery may be performed in a manner that may allow a surgeon to be aware of nerves/nerve roots that may lie within the treatment area. This is important because neural tissue may often be visually indistinguishable from surrounding tissue, thus traditional visual methods of guidance and control may be ineffective. In this manner, using the above-described system, care may be taken to avoid manipulating neural tissue (either intentionally or inadvertently) in a manner that may injure one or more nerves and/or result in long-term paralysis. Said another way, the described system may allow the user and/or robotic controller to "see" the nerves within the treatment area using a non-visual and/or indirect sensing means. Once their presence is identified, appropriate care may be taken to avoid inadvertent or unintended contact with them.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

The following clauses present various additional embodiments of the present technology and are intended to be read in light of the preceding disclosure.

Clause 1. A method for detecting an artificially induced neuromuscular response in a subject, the method comprising: receiving, by a processor, a mechanomyography (MMG) output signal from a mechanical sensor in contact with a muscle of the subject; applying, by the processor, one or more conditioning filters to the MMG output signal to generate a conditioned signal; analyzing, by the processor, the conditioned signal to identify one or more candidate waveforms, each candidate waveform meeting one or more analog or digital signal characteristic criteria associated with an artificially induced neuromuscular response; comparing, by the processor, a first candidate waveform to a second candidate waveform to determine a degree of similarity between the first and second candidate waveforms; providing an alert to a user that indicates detection of the artificially induced neuromuscular response when the degree of similarity exceeds a predetermined threshold.

Clause 2. The method of clause 1, further comprising: comparing, by the processor, the first candidate waveform and the second candidate waveform by determining a similarity score between the first and second candidate waveforms.

Clause 3. The method of clause 2, further comprising: outputting the similarity score to the user as a confidence metric indicating a confidence that the first and second candidate waveforms correspond to an artificially induced neuromuscular response.

Clause 4. The method of clause 1, wherein comparing the first candidate waveform and the second candidate waveform comprises: determining, by the processor, one or more characteristics of a parameter space associated with each of the first candidate waveform and the second candidate waveform, the parameter space including one or more of: a maximum amplitude, a minimum amplitude, a waveform duration, a time of occurrence relative to a reference point, a rate of change, or frequency content; computing, by the processor, a degree of similarity between the first candidate waveform and the second candidate waveform based on a comparison of the one or more characteristics of the parameter space associated with each of the first and second candidate waveforms.

Clause 5. The method of clause 1, wherein comparing the first candidate waveform and the second candidate waveform employs a machine learning model trained to recognize patterns within the first and second candidate waveforms that are indicative of an artificially induced neuromuscular response.

Clause 6. The method of clause 5, further comprising: continuously retraining, by the processor, the machine learning model based on newly acquired candidate waveforms to adapt and improve recognition of the patterns indicative of the artificially induced neuromuscular response.

Clause 7. The method of clause 1, further comprising: applying, by the processor, a Fourier transform or a wavelet transform to the conditioned signal prior to identifying the one or more candidate waveforms.

Clause 8. The method of clause 1, further comprising: applying, by the processor, a Fourier transform or a wavelet transform to the first and second candidate waveforms following determination that the degree of similarity between the first and second candidate waveforms exceeds the predetermined threshold.

Clause 9. The method of clause 1, further comprising: preprocessing the MMG output signal prior to identifying the one or more candidate waveforms by applying filtering or artifact removal algorithms to isolate particular components of the MMG output signal.

Clause 10. The method of clause 1, further comprising: postprocessing the first and second candidate waveforms by applying a frequency transform to the first and second candidate waveforms to confirm that frequency content of the first and second candidate waveforms matches an expected frequency profile for the artificially induced neuromuscular response.

Clause 11. The method of clause 1, further comprising: generating, by a processor, a series of electrical stimuli having a variable frequency and transmitting the electrical stimuli to an electrode in contact with tissue of the subject, wherein the MMG output signal corresponds to muscle responses resulting from the variable frequency electrical stimuli; wherein a periodicity between a first and second electrical stimulus is different than a periodicity between the second electrical stimulus and a third electrical stimulus; and wherein comparing the first candidate waveform and the second candidate waveform comprises determining whether a periodicity between the first and second candidate waveforms matches the periodicity between the first and second electrical stimuli.

Clause 12. The method of clause 1, further comprising: outputting, by the processor, a confidence metric indicating a statistical confidence that the first and second candidate waveforms correspond to an artificially induced neuromuscular response, wherein the confidence metric is a function of at least one of: a quantity of identified candidate waveforms, an algorithm used to identify the candidate waveforms, or a comparison between a periodicity of the identified candidate waveforms and a periodicity of applied electrical stimuli.

Clause 13. The method of clause 12, further comprising: refining, by the processor, the confidence metric upon identification of a third candidate waveform meeting the predetermined signal characteristic criteria.

Clause 14. The method of clause 1, further comprising: receiving, by the processor, an indication of a physical movement of the muscle from a mechanical sensor in response to an electrical stimulus from an electrode; determining, by the processor, that the electrical stimulus has a current insufficient to induce a candidate waveform meeting the predetermined signal characteristic criteria; maintaining a prior determined confidence that the first and second candidate waveforms correspond to an artificially induced neuromuscular response.

Clause 15. The method of clause 1, further comprising: detecting, by the processor, a predefined number of sequential candidate waveforms meeting the predetermined signal characteristic criteria; determining, by the processor, a minimum electrical stimulus current required to induce a candidate waveform meeting the predetermined signal characteristic criteria.

Clause 16. The method of clause 15, further comprising: reducing, by the processor, a current of sequential electrical stimuli; monitoring, by the processor, for induced candidate waveforms meeting the predetermined signal characteristic criteria responsive to each electrical stimulus; and identifying a minimum current at which candidate waveforms are no longer detected responsive to the electrical stimuli.

Clause 17. The method of clause 1, further comprising: determining, by the processor, a first minimum electrical stimulus current required to induce a candidate waveform meeting the predetermined signal characteristic criteria at a first time; determining, by the processor, a second minimum electrical stimulus current required to induce a candidate waveform meeting the predetermined signal characteristic criteria at a second time; and detecting, by the processor, a change in health of a nerve innervating the muscle based on a comparison of the first minimum current and the second minimum current.

Clause 18. A system for detecting an artificially induced neuromuscular response in a subject, the system comprising: one or more electrodes configured to transmit electrical stimuli to tissue of the subject at a stimulation site; one or more sensors configured to be placed in proximity to a muscle of the subject and to output a mechanomyography (MMG) signal in response to muscle activity; and a processor configured to: receive the MMG signal from the one or more sensors; analyze the MMG signal to identify candidate waveforms meeting one or more signal criteria indicative of a neuromuscular response; determine a degree of similarity between a first candidate waveform and a second candidate waveform; and provide an alert to a user when the degree of similarity exceeds a predetermined threshold, the alert indicating detection of the artificially induced neuromuscular response.

Clause 19. The system of clause 18, wherein the processor is further configured to determine a confidence metric indicating a statistical confidence that the first and second candidate waveforms correspond to the artificially induced neuromuscular response based on the degree of similarity.

Clause 20. The system of clause 18, further comprising: a robotic surgical system having a robotic arm configured to manipulate a surgical instrument within a body of the subject, wherein the processor is further configured to transmit a control signal to the robotic surgical system when the degree of similarity between candidate waveforms exceeds the predetermined threshold to cause the robotic system to adjust motion of the robotic arm and surgical instrument to avoid contacting neural tissue.

Clause 21. A method for detecting an artificially induced neuromuscular response in a subject during a robotic surgical procedure, the method comprising: receiving, by a processor, a mechanomyography (MMG) output signal from a mechanical sensor in contact with a muscle of the subject;

applying, by the processor, one or more conditioning filters to the MMG output signal to generate a conditioned signal; analyzing, by the processor, the conditioned signal to identify a first candidate waveform and a second candidate waveform, each candidate waveform meeting one or more signal criteria associated with an artificially induced neuromuscular response; determining, by the processor, a degree of similarity between the first candidate waveform and the second candidate waveform exceeds a predetermined threshold; transmitting, by the processor, a control signal to a robotic surgical system in response to determining the degree of similarity exceeds the predetermined threshold, wherein the control signal causes the robotic surgical system to adjust motion of a robotic arm manipulating a surgical instrument to avoid contacting neural tissue; and providing an alert to a user indicating detection of the artificially induced neuromuscular response.

Clause 22. A method for monitoring health of a nerve during a surgical procedure, the method comprising: positioning, by a processor, an electrode in contact with the nerve; transmitting, by the processor, an electrical stimulus to the nerve via the electrode, wherein the electrical stimulus has a current exceeding a threshold current known to induce an artificially-induced neuromuscular response; receiving, by the processor, a mechanomyography (MMG) output signal from a mechanical sensor in contact with a muscle innervated by the nerve; analyzing, by the processor, the MMG output signal to identify a first candidate waveform and a second candidate waveform using one or more signal criteria indicating an artificially-induced neuromuscular response; determining, by the processor, a degree of similarity between the first candidate waveform and the second candidate waveform exceeds a predetermined threshold; determining, by the processor, a minimum electrical stimulus current required to induce a candidate waveform meeting the one or more signal criteria; comparing, by the processor, the minimum electrical stimulus current to a known threshold stimulation current to assess health of the nerve.

Clause 23. A method for detecting an artificially induced neuromuscular response in a subject, the method comprising: generating, by a processor, a series of electrical stimuli having a variable frequency, wherein a first periodicity between a first electrical stimulus and a second electrical stimulus is different than a second periodicity between the second electrical stimulus and a third electrical stimulus; transmitting the series of variable frequency electrical stimuli to an electrode in contact with tissue of the subject; receiving, by the processor, a mechanomyography (MMG) output signal from a mechanical sensor coupled to a muscle of the subject, wherein the MMG output signal corresponds to muscle responses resulting from the variable frequency electrical stimuli; analyzing, by the processor, the MMG output signal to identify a series of candidate waveforms, each candidate waveform meeting one or more signal criteria associated with an artificially induced neuromuscular response; determining, by the processor, a periodicity between a first candidate waveform and a second candidate waveform in the series of candidate waveforms; comparing, by the processor, the determined periodicity between the first and second candidate waveforms to the first periodicity and the second periodicity of the variable frequency electrical stimuli; and providing an alert to a user that indicates detection of the artificially induced neuromuscular response when the determined periodicity matches the first periodicity or the second periodicity within a predefined tolerance.

Clause 24. The method of clause 23, wherein the variable frequency of the electrical stimuli is continuously variable such that the first periodicity is different than the second periodicity and the second periodicity is different than a third periodicity between the third electrical stimulus and a fourth electrical stimulus.

Clause 25. The method of clause 23, wherein analyzing the MMG output signal comprises: applying a wavelet transform to the MMG output signal to determine convolution coefficients indicative of similarities between the MMG output signal and a plurality of wavelets across a plurality of time steps; generating a net-convolution coefficient (NCC) by combining the convolution coefficients at each time step; and identifying peaks in the NCC as the series of candidate waveforms.

Clause 26. The method of clause 25, wherein the determined periodicity between the first and second candidate waveforms corresponds to a number of time steps between identified peaks in the NCC corresponding to the first and second candidate waveforms.

The invention claimed is:

1. A method for detecting an artificially induced neuromuscular response in a subject, the method comprising:
receiving, by a processor, a mechanomyography (MMG) output signal from a mechanical sensor in contact with a muscle of the subject;
applying, by the processor, one or more conditioning filters to the MMG output signal to generate a conditioned signal;
analyzing, by the processor, the conditioned signal to identify one or more candidate waveforms, each candidate waveform meeting one or more analog or digital signal characteristic criteria associated with an artificially induced neuromuscular response;
comparing, by the processor, a first candidate waveform to a second candidate waveform to determine a degree of similarity between the first and second candidate waveforms;
providing an alert to a user that indicates detection of the artificially induced neuromuscular response when the degree of similarity exceeds a predetermined threshold.

2. The method of claim 1, further comprising:
comparing, by the processor, the first candidate waveform and the second candidate waveform by determining a similarity score between the first and second candidate waveforms.

3. The method of claim 2, further comprising:
outputting the similarity score to the user as a confidence metric indicating a confidence that the first and second candidate waveforms correspond to an artificially induced neuromuscular response.

4. The method of claim 1, wherein comparing the first candidate waveform and the second candidate waveform comprises:
determining, by the processor, one or more characteristics of a parameter space associated with each of the first candidate waveform and the second candidate waveform, the parameter space including one or more of:
a maximum amplitude, a minimum amplitude, a waveform duration, a time of occurrence relative to a reference point, a rate of change, or frequency content;
computing, by the processor, a degree of similarity between the first candidate waveform and the second candidate waveform based on a comparison of the one or more characteristics of the parameter space associated with each of the first and second candidate waveforms.

5. The method of claim 1, wherein comparing the first candidate waveform and the second candidate waveform employs a machine learning model trained to recognize patterns within the first and second candidate waveforms that are indicative of an artificially induced neuromuscular response.

6. The method of claim 5, further comprising:
continuously retraining, by the processor, the machine learning model based on newly acquired candidate waveforms to adapt and improve recognition of the patterns indicative of the artificially induced neuromuscular response.

7. The method of claim 1, further comprising:
applying, by the processor, a Fourier transform or a wavelet transform to the conditioned signal prior to identifying the one or more candidate waveforms.

8. The method of claim 1, further comprising:
applying, by the processor, a Fourier transform or a wavelet transform to the first and second candidate waveforms following determination that the degree of similarity between the first and second candidate waveforms exceeds the predetermined threshold.

9. The method of claim 1, further comprising:
preprocessing the MMG output signal prior to identifying the one or more candidate waveforms by applying filtering or artifact removal algorithms to isolate particular components of the MMG output signal.

10. The method of claim 1, further comprising:
postprocessing the first and second candidate waveforms by applying a frequency transform to the first and second candidate waveforms to confirm that frequency content of the first and second candidate waveforms matches an expected frequency profile for the artificially induced neuromuscular response.

11. The method of claim 1, further comprising:
generating, by a processor, a series of electrical stimuli having a variable frequency and transmitting the electrical stimuli to an electrode in contact with tissue of the subject, wherein the MMG output signal corresponds to muscle responses resulting from the variable frequency electrical stimuli;
wherein a periodicity between a first and second electrical stimulus is different than a periodicity between the second electrical stimulus and a third electrical stimulus;
and wherein comparing the first candidate waveform and the second candidate waveform comprises determining whether a periodicity between the first and second candidate waveforms matches the periodicity between the first and second electrical stimuli.

12. The method of claim 1, further comprising:
outputting, by the processor, a confidence metric indicating a statistical confidence that the first and second candidate waveforms correspond to an artificially induced neuromuscular response, wherein the confidence metric is a function of at least one of:
a quantity of identified candidate waveforms, an algorithm used to identify the candidate waveforms, or a comparison between a periodicity of the identified candidate waveforms and a periodicity of applied electrical stimuli.

13. The method of claim 12, further comprising:
refining, by the processor, the confidence metric upon identification of a third candidate waveform meeting the predetermined signal characteristic criteria.

14. The method of claim 1, further comprising:
receiving, by the processor, an indication of a physical movement of the muscle from a mechanical sensor in response to an electrical stimulus from an electrode;
determining, by the processor, that the electrical stimulus has a current insufficient to induce a candidate waveform meeting the predetermined signal characteristic criteria;
maintaining a prior determined confidence that the first and second candidate waveforms correspond to an artificially induced neuromuscular response.

15. The method of claim 1, further comprising:
detecting, by the processor, a predefined number of sequential candidate waveforms meeting the predetermined signal characteristic criteria;
determining, by the processor, a minimum electrical stimulus current required to induce a candidate waveform meeting the predetermined signal characteristic criteria.

16. The method of claim 15, further comprising:
reducing, by the processor, a current of sequential electrical stimuli;
monitoring, by the processor, for induced candidate waveforms meeting the predetermined signal characteristic criteria responsive to each electrical stimulus;
and identifying a minimum current at which candidate waveforms are no longer detected responsive to the electrical stimuli.

17. The method of claim 1, further comprising:
determining, by the processor, a first minimum electrical stimulus current required to induce a candidate waveform meeting the predetermined signal characteristic criteria at a first time;
determining, by the processor, a second minimum electrical stimulus current required to induce a candidate waveform meeting the predetermined signal characteristic criteria at a second time;
and detecting, by the processor, a change in health of a nerve innervating the muscle based on a comparison of the first minimum current and the second minimum current.

18. A system for detecting an artificially induced neuromuscular response in a subject, the system comprising:
one or more electrodes configured to transmit electrical stimuli to tissue of the subject at a stimulation site;
one or more sensors configured to be placed in proximity to a muscle of the subject and to output a mechanomyography (MMG) signal in response to muscle activity;
and a processor configured to:
receive the MMG signal from the one or more sensors;
analyze the MMG signal to identify candidate waveforms meeting one or more signal criteria indicative of a neuromuscular response;
determine a degree of similarity between a first candidate waveform and a second candidate waveform;
and provide an alert to a user when the degree of similarity exceeds a predetermined threshold, the alert indicating detection of the artificially induced neuromuscular response.

19. The system of claim 18, wherein the processor is further configured to determine a confidence metric indicating a statistical confidence that the first and second candidate waveforms correspond to the artificially induced neuromuscular response based on the degree of similarity.

20. The system of claim 18, further comprising:
a robotic surgical system having a robotic arm configured to manipulate a surgical instrument within a body of the subject, wherein the processor is further configured to transmit a control signal to the robotic surgical system when the degree of similarity between candidate waveforms exceeds the predetermined threshold to cause the robotic system to adjust motion of the robotic arm and surgical instrument to avoid contacting neural tissue.

21. A method for monitoring health of a nerve during a surgical procedure, the method comprising:
- positioning, by a processor, an electrode in contact with the nerve;
- transmitting, by the processor, an electrical stimulus to the nerve via the electrode, wherein the electrical stimulus has a current exceeding a threshold current known to induce an artificially-induced neuromuscular response;
- receiving, by the processor, a mechanomyography (MMG) output signal from a mechanical sensor in contact with a muscle innervated by the nerve;
- analyzing, by the processor, the MMG output signal to identify a first candidate waveform and a second candidate waveform using one or more signal criteria indicating an artificially-induced neuromuscular response;
- determining, by the processor, a degree of similarity between the first candidate waveform and the second candidate waveform exceeds a predetermined threshold;
- determining, by the processor, a minimum electrical stimulus current required to induce a candidate waveform meeting the one or more signal criteria;
- comparing, by the processor, the minimum electrical stimulus current to a known threshold stimulation current to assess health of the nerve.

\* \* \* \* \*